(12) United States Patent
Pastan et al.

(10) Patent No.: US 7,129,332 B2
(45) Date of Patent: Oct. 31, 2006

(54) ANTI-EGFRVIII SCFVS WITH IMPROVED CYTOTOXICITY AND YIELD, IMMUNOTOXINS BASED THEREON, AND METHODS OF USE THEREOF

(75) Inventors: Ira Pastan, Potomac, MD (US); Richard Beers, Washington, DC (US); Partha S. Chowdhury, Rockville, MD (US); Darell Bigner, Mebane, NC (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 379 days.

(21) Appl. No.: 10/203,675

(22) PCT Filed: Feb. 23, 2001

(86) PCT No.: PCT/US01/05923
§ 371 (c)(1),
(2), (4) Date: Aug. 9, 2002

(87) PCT Pub. No.: WO01/62931
PCT Pub. Date: Aug. 30, 2001

(65) Prior Publication Data
US 2003/0211097 A1 Nov. 13, 2003

Related U.S. Application Data

(60) Provisional application No. 60/185,039, filed on Feb. 25, 2000.

(51) Int. Cl.
| | |
|---|---|
| *C12P 21/08* | (2006.01) |
| *A61K 39/395* | (2006.01) |
| *C07H 21/04* | (2006.01) |
| *C12P 21/04* | (2006.01) |

(52) U.S. Cl. .............. 530/387.3; 530/388.22; 530/388.8; 530/391.7; 424/133.1; 424/135.1; 424/143.1; 424/155.1; 424/183.1

(58) Field of Classification Search ............. 530/387.1, 530/387.3, 388.1, 388.22, 391.7, 388.8; 536/23.53; 424/133.1, 141.1, 135.1, 143.1, 155.1, 181.1, 424/183.1
See application file for complete search history.

(56) References Cited

U.S. PATENT DOCUMENTS 6,074,644 A * 6/2000 Pastan et al.
6,428,788 B1 * 8/2002 Debinski et al.

OTHER PUBLICATIONS

Kuan et al. Clinical Cancer Research, 5:1539-1549, Jun. 1999.*
Chowdhury et al. Nature Biotechnology, 17:568-572, Jun. 1999.*
Campion et al. The Journal of Biological Chemistry, 268(3):1742-1748, Jan. 25, 1993.*
William E. Paul, Fundamental Immunology, pp. 292-295, 1993.*
Rudikoff et al. Proc. Natl. Acad. Sci. USA, 79:1979-1983, 1982.*
Winter et al. Annual Review of Immunology, 12:433-455, 1994.*
Lorimer et al. Proc. Natl. Acad. Sci. USA, 93(25):14815-14820, Dec. 10, 1996.*
Lorimer, et al., "Directed evolution of higher affinity single chain Fv antibodies specific for the mutani EGF receptor EGFRvIII." *Proceedings of the American Association for Cancer Research*, Mar. 1998, p. 65, vol. 39, Baltimore, MD, USA, XP002176478.

* cited by examiner

*Primary Examiner*—Larry R. Helms
*Assistant Examiner*—David J. Blanchard
(74) *Attorney, Agent, or Firm*—Townsend and Townsend and Crew LLP

(57) ABSTRACT

The invention provides antibodies to a mutant form of the epidermal growth factor receptor known as EGFRvIII found only or primarily on the surface of glioblastoma cells, and on cells of breast, ovarian and non-small cell lung carcinomas. The antibodies provided by the invention have the complementarity determining regions ("CDRs") of the scFv designated MR1, but with mutations at positions 98 and 99 in the CDR3 of the heavy chain variable region and, optionally, in other CDRs. In particular, the invention provides an antibody, designated MR1-1, which mutates MR1 in the CDR3 of the VH and VL chains. The invention provides additional antibodies in which MR1 is mutated in the CDR1 and 2 of VH or VL, or both.

30 Claims, 6 Drawing Sheets

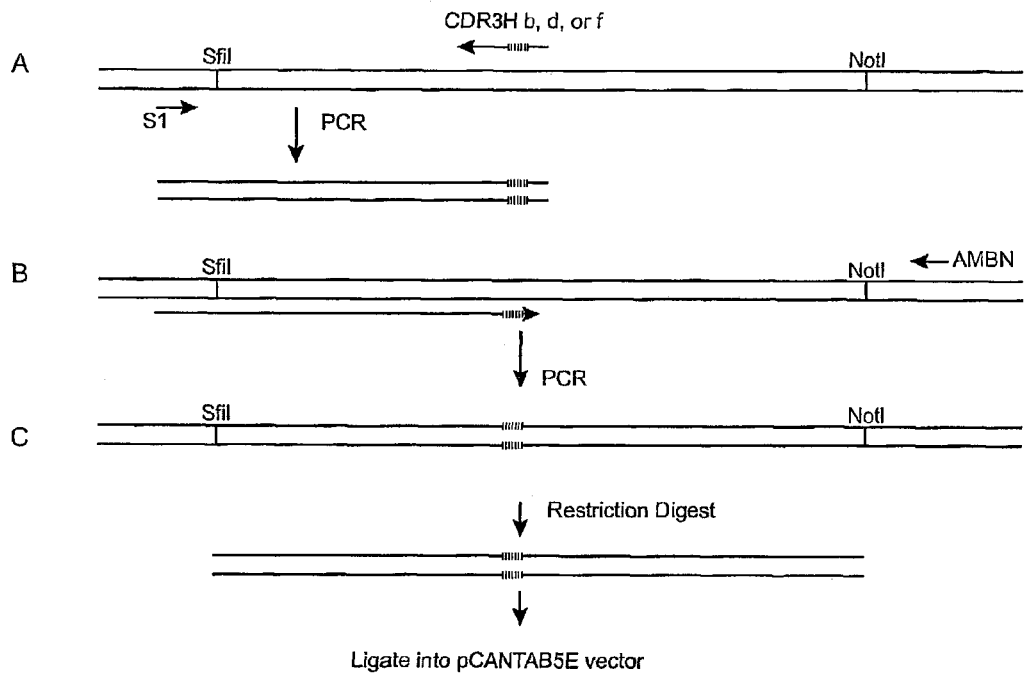

A) pCANTAB5E-MR1 was used as template for amplification using an upstream primer S1, and a downstream primer CDR3H b, d or f, containing degeneracies (NNS) in the targeted areas.

B) pCANTAB5E-MR1 was used as template for amplification using the products of reaction in step A as upstream primers and a downstream primer AMBN.

C) The products from reaction B are digested and cloned into pCANTAB5E.

ANTI-EGFRVIII SCFVS WITH IMPROVED CYTOTOXICITY AND YIELD, IMMUNOTOXINS BASED THEREON, AND METHODS OF USE THEREOF

CROSS-REFERENCES TO RELATED APPLICATIONS

This application is a national stage filing under 35 U.S.C. § 371 of international application PCT/US01/05923, filed Feb. 23, 2001, and claims the benefit of U.S. Provisional Patent Application No. 60/185,039, filed Feb. 25, 2000.

STATEMENT AS TO RIGHTS TO INVENTIONS MADE UNDER FEDERALLY SPONSORED RESEARCH AND DEVELOPMENT

Not applicable.

BACKGROUND OF THE INVENTION

A mutant form of the epidermal growth factor receptor, designated "EGFRvIII," is highly expressed in some 50–60% of glioblastomas and has also been shown to be present in some 70–80% of carcinomas of the breast and ovary, and about 16% of non-small cell lung carcinomas (Wikstrand et al., Cancer Res. 55:3140–3148 (1995); Moscatello et al., Cancer Res. 55:5536–5539 (1995)). The mutation consists of an in-frame deletion of exons 2–7 near the amino terminus of the extracellular domain which results in the expression of an EGFR mRNA with an 801 base deletion. The mutant protein contains a new glycine codon at the splice junction (Moscatello et al., supra). The mutant receptor is expressed on the cell surface and creates a new tumor specific cell surface epitope (sequence) at the deletion junction. The receptor has constitutive tyrosine kinase activity that enhances the tumorigenicity of glioblastomas in vivo (Nishikawa et al., Proc. Natl. Acad. Sci. USA 91:7727–7731 (1994)). Because of the tumor-specific extracellular sequence, the mutant receptor is an attractive potential target for cancer therapy, particularly via the use of immunotoxins.

Immunotoxins are made by fusing a targeting moiety, such as an antibody or a portion of an antibody, to a protein toxin such as Pseudomonas exotoxin. Immunotoxins have been demonstrated to have activity against solid tumors in humans, as demonstrated by a Phase I clinical trial in which an immunotoxin made with an antibody specific for a Lewis Y-related antigen overexpressed on many tumors showed tumor regression (Pai et al., Nat Med. 2:350–353 (1996)). Immunotoxins such as the one in the Pai et al., study, which was made with a whole mouse monoclonal antibody, however, have certain disadvantages. They are relatively large, which limits their tumor penetration. Further, there is frequently heterogeneity of the linkage between the antibody and the toxin, and it is difficult to produce the conjugates in large quantity. Similarly, the various antibodies against EGFRvIII known in the art, as exemplified by U.S. Pat. No. 5,212,290, WO 96/16988, and Reist et al., Cancer Res. 55:4375–4382 (1995), have limitations for constructing immunotoxins. Attempts to overcome these problems by making wholly recombinant immunotoxins in which cloned Fvs are used for targeting have been hampered because most antibody variable domains function poorly as Fvs, either because of instability due to weak $V_H$-$V_L$ association or because of poor binding affinity.

MR1 is a single chain antibody variable domain (scFv) that binds specifically to EGFRvIII. The MR1 scFV was isolated from an antibody phage display library (Lorimer et al., Proc. Natl. Acad. Sci. USA 93:14815–14820 (1996)). The scFv library containing MR1 was prepared from the splenic mRNA of a mouse which was immunized with an EGFRvIII specific peptide plus the extracellular domain of EGFRvIII purified by affinity chromatography from EGFRvIII-expressing tumor xenografts (Lorimer et al., Clin. Cancer Res. 1:859–864 (1995)). MR1 was developed as a prospect for developing a therapeutic agent which would be specifically targeted to EGFRvIII-positive cancer cells. The sequence of MR1 has been deposited in GenBank under Accession Number U76382 (the nucleic acid sequence shown under this Accession Number is set forth as SEQ ID NO:17, and the amino acid sequence is set forth as SEQ ID NO.:18).

Immunotoxin MR1(Fv)-PE38 was constructed by fusing the scFv of MR1 to a truncated form of Pseudomonas exotoxin A, PE38, in which all of domain Ia and amino acids 365–380 of domain Ib have been deleted (Lorimer et al., Proc. Natl. Acad. Sci. USA 93:14815–14820 (1996). Several other recombinant PE38 immunotoxins are now in clinical trials (Kreitman et al., Blood 94(10):3340–48 (1999); Pai-Scherf et al., Clin. Cancer Res. (in press) (1999); Pai et al., Clin. Application Immunotoxins 234:83–96 (1998)). Generally, the scFv genes are joined with the PE38 gene by a short linker and cloned into a T7-based expression vector. The recombinant immunotoxins are expressed in E. coli, where they accumulate in inclusion bodies. After the inclusion bodies are washed extensively, they are dissolved in guanidine hydrochloride and the protein renatured and purified by ion-exchange chromatography and gel filtration. The resulting molecules are active and are directed to a cell specific antigen by the scFv. Cell death is caused by the activity of the toxin.

To be useful as therapeutic agents, immunotoxins should have a high affinity for the antigen, resulting in high cytotoxicity toward cells expressing the antigen. To ease processing and cost concerns, it is also advantageous if the immunotoxin can be produced with a high yield. MR1 (scFv)-PE38 is the highest affinity, most cytotoxic immunotoxin available against cells expressing EGFRvIII, but it is far from ideal. It has a Kd of 8 nM and a yield of less than 3%. It would therefore be advantageous to develop antibodies which bind to EGFRvIII with greater affinity, and which, when coupled to PE38 or other toxins, form immunotoxins with higher cytotoxicity to EGFRvIII-expressing cells. Additionally, it would be helpful to find antibodies which form immunotoxins with higher yields.

Several attempts to solve these problems by developing additional scFv from monoclonal anti-EGFRvIII antibodies failed. MR1 remains the only scFv available in the art for targeting anti-EGFRvIII immunotoxins.

SUMMARY OF THE INVENTION

In one aspect, the invention provides antibodies with improved binding for the mutant form of the epidermal growth factor receptor known as EGFRvIII. In particular, the invention provides polypeptides with a mutated antibody variable heavy ($V_H$) chain regions or a mutated light chain ($V_L$) region, or both, which polypeptide has a Kd for EGFRvIII of 7 nM, 6 nM, 5 nM, 4 nM, 3.5 nM, 3 nM, or lower, the mutated $V_H$ or $V_L$ having a sequence that differs from parental antibody MR1 $V_H$ or $V_L$, respectively, by an amino acid substitution of at least one amino acid in a complementarity determining region (CDR), the amino acid encoded by a codon that comprises a nucleotide belonging to a hot spot motif selected from AGY or RGYW, wherein R is A or G, Y is C or T, and W is A or T. In some embodiments, the substitution can occur in the CDR3 $V_H$ or the CDR3 $V_L$. In other embodiments, substitutions can occur in the CDR1 $V_H$ or CDR2 $V_H$, or both, or in the CDR1 $V_L$ or CDR2 $V_L$, or both, or in any combination of the CDR1, 2, and 3 $V_H$ and $V_L$. For example, in one embodiment, substitutions can occur in the CDR3 $V_L$, the CDR2 $V_L$, and the CDR1 $V_H$.

In a preferred embodiment, the polypeptide has a substitution in the CDR3 $V_H$ of at least one amino acid selected from the group consisting of S98 and T99. In other preferred embodiments, the substitutions are selected from P98-Y99, P98-N99, P98-W99, P98-I99, P98-F99, and P98-V99. The polypeptide can further have a substitution in the CDR3 VL wherein W is substituted for F at position 92. In a particularly preferred embodiment, the polypeptide has substitutions in the heavy chain of S98P-T99Y and in the light chain comprises the substitution F92W (defining the antibody designated "MR1-1").

The polypeptides described above can be a single-chain variable region of an antibody (an "scFv"), a disulfide stabilized Fv, a Fab, a F(ab')$_2$, or other fragment of an antibody which retains the ability to recognize and bind to an antigen. They can also comprise a surface protein of a bacteriophage.

In preferred embodiments, the polypeptides described above have a Kd for EGFvIII at least 1 nM lower than that of MR1. The polypeptides can have a Kd of 7, 6, 5, 4, 3.5, 3 or lower.

The polypeptides described above can also be coupled, attached or otherwise linked to an effector molecule, therapeutic moiety, or detectable label. The therapeutic moiety can be a toxin or a cytotoxic portion of a toxin (a "toxic moiety"), which in conjunction with the polypeptide forms an immunotoxin. The toxic moiety can be Diphtheria toxin or a cytotoxic fragment thereof, saporin, pokeweed antiviral protein, ricin or a cytotoxic fragment thereof, and bryodin 1. In preferred embodiments, the toxin is a *Pseudomonas* exotoxin ("PE") or a cytotoxic fragment of a PE. In particularly preferred embodiments, the PE is PE38. The immunotoxins formed by the combination of the polypeptide and the toxic moiety can have an IC$_{50}$ of 7 ng/ml of lower, 6 ng/ml or lower, 5 ng/ml or lower, 4 ng/ml or lower, or of or about 3.5 ng/ml or lower. The immunotoxin can have a yield when recombinantly expressed of at least 3%, and can be 4%, 5%, 6%, 7%, 8%, 9% 10%, or higher.

The invention further provides nucleic acid molecules encoding polypeptides with a mutated antibody variable heavy ($V_H$) chain regions or a mutated light chain ($V_L$) region, or both, which polypeptide has a Kd for EGFRvIII of 7 nM or lower, the mutated $V_H$ or $V_L$ having a sequence that differs from parental antibody MR1 $V_H$ or $V_L$, respectively, by an amino acid substitution of at least one amino acid in a complementarity determining region (CDR), the amino acid encoded by a codon that comprises a nucleotide belonging to a hot spot motif selected from AGY or RGYW, wherein R is A or G, Y is C or T, and W is A or T. In some embodiments, the substitution can occur in the CDR3 $V_H$ or the CDR3 $V_L$. In other embodiments, substitutions can occur in the CDR1 $V_H$ or CDR2 $V_H$, or both, or in the CDR1 $V_L$ or CDR2 $V_L$, or both, or in any combination of the CDR1, 2, and 3 $V_H$ and $V_L$. For example, in one embodiment, substitutions can occur in the CDR3 $V_L$, the CDR2 $V_L$, and the CDR1 $V_H$.

In a preferred embodiment, the nucleic acid molecule encodes a polypeptide having a substitution in the CDR3 $V_H$ compared to MR1 of at least one amino acid selected from the group consisting of S98 and T99. In other preferred embodiments, the substitutions are selected from P98-Y99, P98-N99, P98-W99, P98-I99, P98-F99, and P98-V99. The nucleic acid molecule can also encode a polypeptide having a substitution in the CDR3 $V_L$ compared to MR1 comprising a W substituted for a F at position 92.

The nucleic acid molecules can encode polypeptides which are a single-chain variable region of an antibody (an "scFv"), a disulfide stabilized Fv, a Fab, a F(ab')$_2$, or other fragment of an antibody which retains the ability to recognize and bind to an antigen. The polypeptides can also comprise a surface protein of a bacteriophage. The nucleic acid molecules described above can be operably linked to a promoter.

In another set of embodiments, the invention provides methods of killing a cell bearing an antigen, comprising contacting the cell with an immunotoxin comprising a toxic moiety and a targeting moiety, the targeting moiety comprising a polypeptide with a mutated antibody variable heavy ($V_H$) chain regions or a mutated light chain ($V_L$) region, or both, which polypeptide has a Kd for EGFRvIII of 7 nM or lower, the mutated $V_H$ or $V_L$ having a sequence that differs from parental antibody MR1 $V_H$ or $V_L$, respectively, by an amino acid substitution of at least one amino acid in a complementarity determining region (CDR), the amino acid encoded by a codon that comprises a nucleotide belonging to a hot spot motif selected from AGY or RGYW, wherein R is A or G, Y is C or T, and W is A or T. In some embodiments, the substitution can occur in the CDR3 $V_H$ or the CDR3 $V_L$. In other embodiments, substitutions can occur in the CDR1 $V_H$ or CDR2 $V_H$, or both, or in the CDR1 $V_L$ or CDR2 $V_L$, or both, or in any combination of the CDR1, 2, and 3 $V_H$ and $V_L$.

In a preferred embodiment, the method comprises a targeting moiety in comprises a polypeptide having a substitution in the CDR3 $V_H$ of at least one amino acid selected from the group consisting of S98 and T99. In other preferred embodiments, the targeting moiety comprises a polypeptide comprising substitutions selected from P98-Y99, P98-N99, P98-W99, P98-I99, P98-F99, and P98-V99. In a particularly preferred embodiment, the targeting moiety is MR1-1.

The targeting moiety can be a single-chain variable region of an antibody (an "scFv"), a disulfide stabilized Fv, a Fab, a F(ab')$_2$, or other fragment of an antibody which retains the ability to recognize and bind to an antigen.

The cell bearing the antigen can be a malignant cell, such as a glioma cell, a breast carcinoma cell, a lung carcinoma cell, or an ovarian carcinoma cell.

BRIEF DESCRIPTION OF THE DRAWINGS

FIG. 1. FIG. 1 shows the strategy for PCR construction of mutant libraries. A. pCANTAB5E-MR1 was used as template for amplification using an upstream primer, S1, and a downstream primer CDR3H b, d, or f, containing degeneracies (NNS) in the targeted areas. B. pCANTAB5E-MR1 was used as template for amplification using the products of reaction in step A as upstream primers and a downstream primer AMBN. C. The products from reaction B are digested and cloned into pCANTAB5E.

DETAILED DESCRIPTION

I. Introduction

Figure 2:
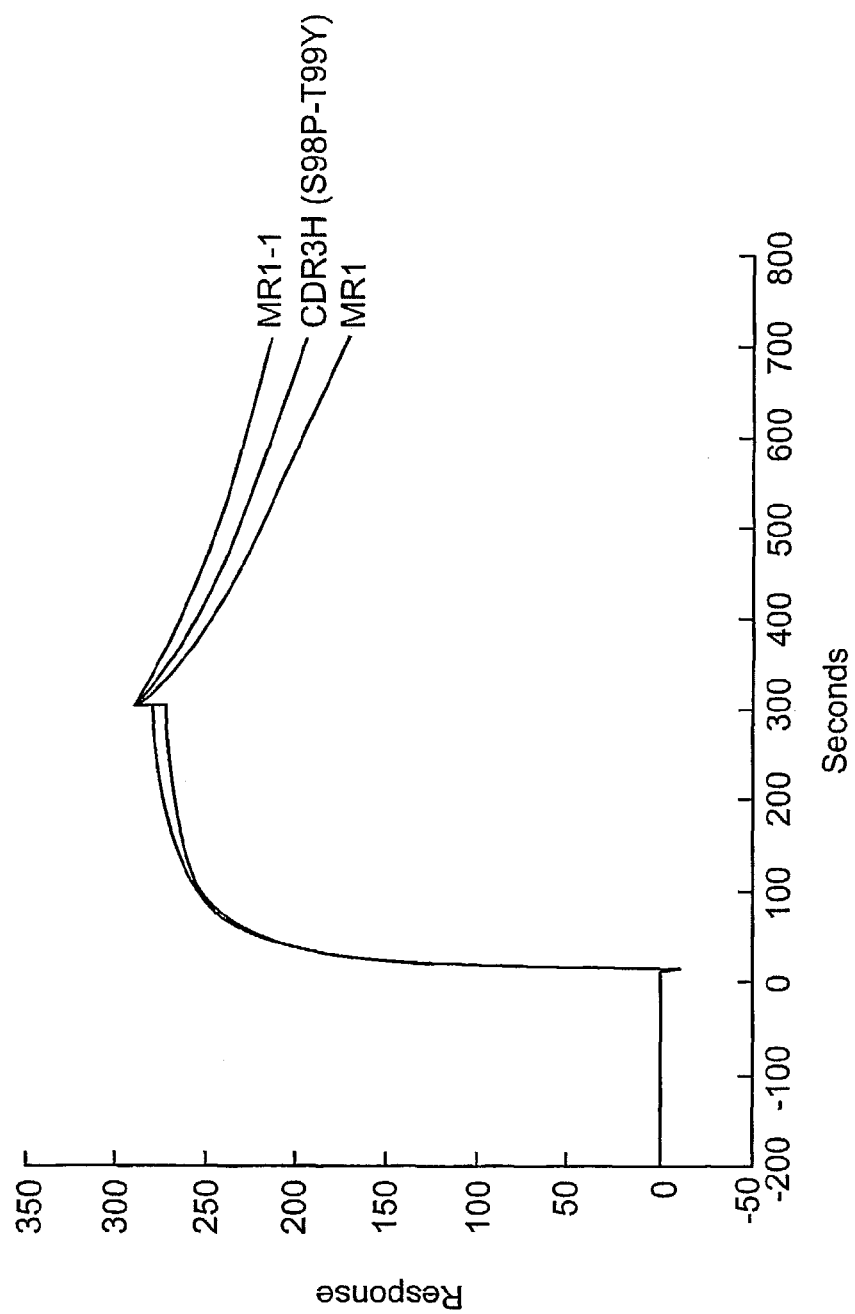
FIG. 2. BIAcore sensorgram of MR1, MR1-1, and MR1 with S98P-T99Y mutations in VH CDR3.

The present invention provides scFv antibodies and other antibodies with higher affinity for EGFRvIII than that of MR1. It further provides immunotoxins with higher cytotoxicity for EGFRvIII-expressing cells than that of the same immunotoxins using MR1 as the targeting portion of the molecule. The antibodies are created from MR1, but are mutated in hot spot regions of their complementarity determining regions (CDRs). Surprisingly, immunotoxins incorporating these mutated forms of MR1 as the targeting moiety not only have high affinity for EGFRvIII, but also can be produced at significantly higher yields than similar immunotoxins employing MR1 as the targeting portion of the molecule.

The limiting factor in the construction of antibody libraries with randomizations in the CDRs is the large number of residues that constitute the CDRs. Because x-ray structures are not available for most antibodies, usually there is no attempt to identify the few CDR residues where mutations are likely to yield higher affinity variants. Consequently, it is necessary to construct extremely large randomized libraries to ensure the isolation of higher affinity variants.

In exemplary studies, mutations were made in CDR3 of the heavy chain variable region ($V_H$) of MR1. The $V_H$ CDR3 of MR1 has eleven amino acid residues. The final two residues of the $V_H$ region, D101 and Y102, were excluded from the mutagenesis studies because they were considered unlikely to participate in antigen binding, for two reasons. First, these two residues usually lie at the interface with the $V_L$ chain. As a result, they are not exposed. Second, these residues are contributed to by the J segment and follow the 3'-junctional region of the $V_H$CDR2. As a result, they are relatively more conserved than the rest of the $V_H$CDR3.

The other nine amino acids at each position of the CDR3 $V_H$ were substituted by each of the other natural amino acids. The studies showed that only mutations in regions known to be hot spots (regions known to undergo hypermutation during antibody affinity maturation, best characterized by the motifs RGYW and AGY, where R is A or G, Y is C or T, and W is A or T) resulted in antibodies with higher cytotoxicity than the parental antibody MR1. The mutations were also found to enhance the yield of immunotoxin when these mutated scFv were incorporated into immunotoxins, compared to a like immunotoxin made with the parental MR1 scFv. In further exemplary studies, mutations were made in the MR1 CDR3 of the light chain variable region. In these studies, mutations were made only to amino acids within a hot spot. Once again, the mutations resulted in antibodies with higher cytotoxicity and yield than the parental antibody MR1.

Based on these results, it is not necessary to randomize every residue in a CDR to identify those where mutations will yield higher affinity variants. It is expected that mutations in the hot spots of $V_H$ and $V_L$ CDRs 1 and 2 will likewise result in antibodies with improved affinity for EGFRvIII, improved cytotoxicity for EGFRvIII-expressing cells when incorporated into immunotoxins, and improved yield for immunotoxins incorporating such scFvs compared to MR1-based immunotoxins. Since the improved properties are due to the substitutions of the amino acids, the same positive effects will also be found when these mutated forms of MR1 (including those mutated in the $V_H$ and $V_L$ CDR3) are incorporated into disulfide stabilized Fvs (dsFvs), or into Fab', F(ab')$_2$, or Fab.

Increased cytotoxic activity does not necessarily correlate with increased affinity (Tables 4 and 5, infra). There is no obvious explanation for this lack of correlation. Besides binding affinity, which is typically measured at 22° C., there are many aspects in the toxicity process which could be affected by the "hot spot" mutations. Such aspects include stability at 37° C., rate of internalization, proteolytic processing and transfer to the compartment required for translocation. It is possible that one or more of these aspects is affected. Antibodies with higher affinity for EGFRvIII are, however, useful for a variety of purposes, and especially for diagnostic uses and in vitro assays to determine the presence or absence of EGFRvIII-expressing cells in a sample. For example, for in vitro uses, antibodies such as scFv with higher affinity for EGFRvIII can be conjugated to radionuclides or to any of a number of other detectable labels and used to detect the presence of cells expressing EGFRvIII in a biopsy sample from a patient to determine whether the patient has a cancer characterized by the presence of such cells, or to determine that the cancer has not yet been eradicated from a patient known to have such a cancer. Similarly, in in vivo uses, scFv, dsFv, or other antibodies of the invention can be conjugated to radionuclides or other detectable labels and used to detect the presence of cells expressing EGFRvIII in the patient, thereby again diagnosing whether the patient has a cancer characterized by the presence of such cells, or that the cancer has not yet been eradicated from a patient known to have such a cancer.

Finally, one striking difference observed among the CDR mutants was the final yield of active monomeric protein. Recombinant toxins accumulate in inclusion bodies as insoluble aggregated protein (immunotoxin). Active monomers are produced by dissolving the inclusion bodies in 6M Guanidine HCl, followed by controlled renaturation in a redox system and separation of monomers from multimers and aggregates. The studies showed that mutations in 1 or 2 amino acids in the CDRs can greatly increase yields (Table 6) of immunotoxin, as defined and explained below. The yield of MR1(Fv)-PE38 is only 2%, but it was dramatically increased to 17% with heavy chain CDR3 S98P-T99S mutations. Presumably, these mutations have a profound effect on the folding pathway. In general, all the heavy chain mutants isolated in the initial mutagenesis of the heavy chain had a better yield than the parental MR1. Thus, the heavy chain of CDR3 is very important for proper folding and the phage expression system may select in some way for proteins that fold more efficiently. Consequently, phage containing better folding Fvs appear to be present in larger numbers and are preferentially enriched during panning on antigen.

Based on these results, it can be expected that phage display can be used to select Fvs mutated in the CDR1 or 2 of the $V_H$ and $V_L$ chains which likewise exhibit an increased production yield compared to the parental MR1 scFv.

In vivo tests were conducted to determine the effect of exemplary immunotoxins targeted by MR1-1 on animal models of human tumors. To establish the tumors, athymic rats and mice were injected intracranially, intrathecally, or subcutaneously with cells of a human gliablastoma cell line (U87MG) which was transfected to express EGFRvIII (the transfected EGFRvIII-expressing cell line is designated U87MG.ΔEGFRvIII and is described by Nishikawa et al., Proc Natl Acad Sci (USA) 91(16):7727–7731 (1994)). Once the tumors were established, the rats or mice were treated with bolus injections or continuous infusions of various doses of immunotoxin. As described in the Examples, below, and FIGS. 3–6, regardless of the tumor location and method of administering the immunotoxin, animals given the immunotoxin at doses of 1 or 2 μg showed markedly less tumor growth, and longer survival times, than that of animals given a saline control.

II. Definitions

Units, prefixes, and symbols are denoted in their Systeme International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more filly defined by reference to the specification in its entirety.

Residues mutated from a known sequence are designated by convention by listing in single letter code the residue normally found at a designated position in the sequence, the position in the sequence of the residue mutated, and the residue substituted for the original residue. Thus, with regard to the MR1 CDR3 $V_H$, the term "S98P" indicates that the serine normally found at position 98 of the normal CDR3 heavy chain of MR1 has been mutated to proline. A designation such as "S98" in which the number is not followed by a designation of an residue references either the residue normally found at that position of the normal sequence of the peptide or that that specific residue is now present at that position (i.e., that the residue designated has been substituted for the residue normally present at that position). Which use is intended herein will be clear by the context. References herein to particular numbered amino acid residues of MR1-1 refer to residues numbered according to Kabat et al., SEQUENCES OF PROTEINS OF IMMUNOLOGICAL INTEREST, U.S. Department of Health and Human Services, (1987), as updated; this reference is hereafter referred to as "Kabat," the contents of which are hereby incorporated by reference) when the sequence of the scFv is aligned and numbered according to the Kabat system.

"EGFRvIII" means a mutant form of the epidermal growth factor receptor recognized by MR1 scFv and characterized by an 801 base pair in frame deletion of exons 2–7 near the amino terminal. This form of the receptor is known in the art, as exemplified by the Wickstrand et al., Moscatello et al., and Lorimer et al. references cited in the Background. Due to a change in terminology, EGFRvIII was originally termed a Type II mutation in some earlier work in the field, as exemplified by U.S. Pat. No. 5,212,290.

As used herein, "antibody" includes reference to an immunoglobulin molecule immunologically reactive with a particular antigen, and includes where appropriate both polyclonal and monoclonal antibodies. The term also includes genetically engineered forms such as chimeric antibodies (e.g., humanized murine antibodies), heteroconjugate antibodies (e.g., bispecific antibodies). The term particularly refers herein to recombinant single chain Fv fragments (scFv), disulfide stabilized (dsFv) Fv fragments (see, U.S. Ser. No. 08/077,252, incorporated herein by reference), or pFv fragments (see, U.S. Provisional Patent Application Nos. 60/042,350 and 60/048,848). The term "antibody" also includes antigen binding forms of antibodies, including fragments with antigen-binding capability (e.g., Fab', $F(ab')_2$, Fab, Fv and rIgG. See also, Pierce Catalog and Handbook, 1994–1995 (Pierce Chemical Co., Rockford, Ill.). See also, e.g., Kuby, J., *Immunology*, 3rd Ed., W.H. Freeman & Co., New York (1998). Which particular sense or senses of the term are intended will be clear in context.

An antibody immunologically reactive with a particular antigen can be generated by recombinant methods such as selection of libraries of recombinant antibodies in phage or similar vectors, see, e.g., Huse et al., *Science* 246:1275–1281 (1989); Ward et al., *Nature* 341:544–546 (1989); and Vaughan et al., *Nature Biotech.* 14:309–314 (1996), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain four "framework" regions interrupted by three hypervariable regions, also called "complementarity-determining regions" or "CDRs". The extent of the framework regions and CDRs have been defined (see, Kabat, supra). The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "VH" refer to the variable region of an immunoglobulin heavy chain of an antibody, including the heavy chain of an Fv, scFv, dsFv or Fab. References to "$V_L$" or a "VL" refer to the variable region of an immunoglobulin light chain, including the light chain of an Fv, scFv, dsfv or Fab.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

The term "linker peptide" includes reference to a peptide within an antibody binding fragment (e.g., Fv fragment) which serves to indirectly bond the variable domain of the heavy chain to the variable domain of the light chain.

The term "parental antibody" generally refers to an antibody of interest which is to be mutated or varied to obtain antibodies or fragments thereof which bind to the same epitope as the parental antibody. As used herein, the term "parental antibody" refers to the scFv designated as "MR1" (GenBank Accession Number U76382) unless otherwise indicated or required by context.

The term "hotspot" means a portion of a nucleotide sequence of a CDR or of a framework region of a variable domain which is a site of particularly high natural mutation. Although CDRs are themselves considered to be regions of hypervariability, it has been learned that mutations are not evenly distributed throughout the CDRs. Particular sites, or hotspots, have been identified as these locations which undergo concentrated mutations. The hotspots are characterized by a number of structural features and sequences. These "hotspot motifs" can be used to identify hotspots. Two consensus sequence motifs which are especially well characterized are the tetranucleotide sequence RGYW and the serine sequence AGY, where R is A or G, Y is C or T, and W is A or T.

A "targeting moiety" or "targeting molecule" is the portion of an immunoconjugate which has the ability to target the immunoconjugate to cells of interest. Typically, the targeting moiety is an antibody, a scFv, a dsFv, a Fab, or a $F(ab')_2$ which recognizes a specific antigen on the cells of interest.

A "toxic moiety" is a cytotoxin or a portion of a cytotoxin which, when incorporated into an immunotoxin, renders the immunotoxin cytotoxic to cells of interest.

An "immunotoxin" is a molecule comprising a targeting molecule, such as an scFv, and a toxic moiety, such as a *Pseudomonas* exotoxin ("PE") or cytotoxic fragment thereof.

Immunotoxins discussed herein are typically expressed as inclusion bodies in *E. coli*, after which the inclusions bodies are purified, solubilized in 6 M guanidine HCl, and the protein refolded. As used herein, the term "yield" refers to the amount of properly folded monomeric immunotoxin collected through this procedure. It is expressed as a percentage determined as: milligrams of protein after MonoQ ion-exchange chromatography/milligrams inclusion body protein refolded.

A "therapeutic moiety" is the portion of an immunoconjugate intended to act as a therapeutic agent.

The term "therapeutic agent" includes any number of compounds currently known or later developed to act as anti-neoplastics, anti-inflammatories, cytokines, anti-infectives, enzyme activators or inhibitors, allosteric modifiers, antibiotics or other agents administered to induce a desired therapeutic effect in a patient. The therapeutic agent may also be a toxin or a radioisotope, where the therapeutic effect intended is, for example, the killing of a cancer cell.

A "detectable label" means, with respect to an immunoconjugate, a portion of the immunoconjugate which has a property rendering its presence detectable. For example, the immunoconjugate may be labeled with a radioactive isotope which permits cells in which the immunoconjugate is present to be detected in immunohistochemical assays.

The terms "effector moiety" and "effector molecule" mean the portion of an immunoconjugate intended to have an effect on a cell targeted by the targeting moiety or to identify the presence of the immunoconjugate. Thus, the effector moiety can be, for example, a therapeutic moiety, a toxin, a radiolabel, or a fluorescent label.

The term "immunoconjugate" means a chimeric molecule comprising a targeting molecule (such as a scFv) attached directly (for example, through a covalent linkage) or indirectly (for example, through a linker peptide) to an effector molecule. In a subset of immunoconjugates, the effector molecule is a toxin, and the chimeric molecule is then more specifically termed an "immunotoxin."

The terms "effective amount" or "amount effective to" or "therapeutically effective amount" includes reference to a dosage of a therapeutic agent sufficient to produce a desired result, such as inhibiting cell protein synthesis by at least 50%, or killing the cell.

The term "toxin" includes reference to abrin, ricin, *Pseudoinonas* exotoxin (PE), diphtheria toxin (DT), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin (e.g., domain Ia of PE or the B chain of DT) and replacing it with a different targeting moiety, such as an antibody.

The term "$IC_{50}$" refers to the concentration of a toxin or immunotoxin (expressed as ng/ml) required to inhibit protein synthesis by 50%.

The term "contacting" includes reference to placement in direct physical association.

An "expression plasmid" comprises a nucleotide sequence encoding a molecule of interest, which is operably linked to a promoter.

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The amino acids and analogs referred to herein are described by shorthand designations as follows in Table 1:

TABLE 1

Amino Acid Nomenclature

| Name | 3-letter | 1-letter |
| --- | --- | --- |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution," when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups in Table 2 each contain amino acids that are typically conservative substitutions for one another:

TABLE 2

1) Alanine (A), Serine (S), Threonine (T);
2) Aspartic acid (D), (Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, *PROTEINS*, W.H. Freeman and Company, New York (1984). It should be noted, however, that while phenylalanine and tryptophan are generally considered to be conservative substitutions for one another, the substitution of tryptophan for phenylalanine in the hot spot of the $V_L$ CDR3 of scFv MR1 created an immunotoxin that was more active than its parent scFv. Accordingly, while these amino acids are considered conservative substitutions for portions of an antibody outside of a CDR, in the context of this invention, these two amino acids are not conservative substitutions for one another within a hot spot. Based on these results, no amino acid substitutions within a hot spot can be considered to be conservative substitutions unless they are tested by, for example, the assays set forth herein, to determine whether or not they affect the binding affinity of the resulting molecule, the yield of an immunotoxin made with that molecule as the targeting moiety, or both.

The terms "substantially similar" in the context of a peptide indicates that a peptide comprises a sequence with at least 90%, preferably at least 95% sequence identity to the reference sequence over a comparison window of 10–20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The phrase "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1–2 kcal/mol for a hydrogen bond. In the context of this invention, the cysteines which form the disulfide bond are within the framework regions of the single chain antibody and serve to stabilize the conformation of the antibody.

The terms "conjugating," "joining," "bonding" or "linking" refer to making two polypeptides into one contiguous polypeptide molecule. In the context of the present invention, the terms include reference to joining an antibody moiety to an effector molecule (EM). The linkage can be either by chemical or recombinant means. Chemical means refers to a reaction between the antibody moiety and the effector molecule such that there is a covalent bond formed between the two molecules to form one molecule.

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are not found within the native form, or express native genes that are otherwise abnormally expressed, underexpressed or not expressed at all.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof as well as conservative variants, i.e., nucleic acids present in wobble positions of codons and variants that, when translated into a protein, result in a conservative substitution of an amino acid.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Nat'l Acad. Sci. USA* 82:2306–2309 (1985)), or the ciliate *Macronucleus*, may be used when the nucleic acid is expressed in using the translational machinery of these organisms.

The phrase "fusing in frame" refers to joining two or more nucleic acid sequences which encode polypeptides so that the joined nucleic acid sequence translates into a single chain protein which comprises the original polypeptide chains.

As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of the expression vector. Host cells may be prokaryotic cells such as *E. coli*, or eukaryotic cells such as yeast, insect, amphibian, or mammalian cells.

The phrase "phage display library" refers to a population of bacteriophage, each of which contains a foreign cDNA recombinantly fused in frame to a surface protein. After replication in a bacterial host, typically *E. coli*, the phage which contain the foreign cDNA of interest are selected by the expression of the foreign protein on the phage surface.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. A number of programs for such alignments are known in the art.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The term "in vivo" includes reference to inside the body of the organism from which the cell was obtained. "Ex vivo" and "in vitro" means outside the body of the organism from which the cell was obtained.

The phrase "malignant cell" or "malignancy" refers to tumors or tumor cells that are invasive and/or able to undergo metastasis, i.e., a cancerous cell.

As used herein, "mammalian cells" includes reference to cells derived from mammals including humans, rats, mice, guinea pigs, chimpanzees, or macaques. The cells may be cultured in vivo or in vitro.

The term "selectively reactive" refers, with respect to an antigen, the preferential association of an antibody, in whole or part, with a cell or tissue bearing that antigen and not to cells or tissues lacking that antigen. It is, of course, recognized that a certain degree of non-specific interaction may occur between a molecule and a non-target cell or tissue. Nevertheless, selective reactivity, may be distinguished as mediated through specific recognition of the antigen. Although selectively reactive antibodies bind antigen, they may do so with low affinity. On the other hand, specific binding results in a much stronger association between the antibody and cells bearing the antigen than between the bound antibody and cells lacking the antigen. Specific binding typically results in greater than 2-fold, preferably greater than 5-fold, more preferably greater than 10-fold and most preferably greater than 100-fold increase in amount of bound antibody (per unit time) to a cell or tissue bearing EGFRvIII as compared to a cell or tissue lacking EGFRvIII. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, ANTIBODIES, A LABORATORY MANUAL, Cold Spring Harbor Publications, New York (1988), for a description of immunoassay formats and conditions that can be used to determine specific immunoreactivity.

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. Preferably, the immunologically reactive conditions employed in the methods of the present invention are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

III. Creation of Antibodies with Higher Affinity for EGFRvIII than that of MR1

Antibodies bind to antigens via residues in their CDRs. Consequently, mutagenesis of CDRs is widely used to improve the affinity of Fab and Fv fragments of antibodies. There are a number of different approaches to CDR mutagenesis. Most of these, such as codon-based mutagenesis (Yelton et al., *J. Immunol.* 155:1994–2004 (1995)), CDR walking (Barbas et al., *Trends Biotech.* 14:230–234 (1996); Yang et al., *J. Mol. Biol.* 254:392–403 (1995)), error prone replication (Low et al., *J. Mol. Biol.* 260:359–368 (1996)) and synthetic CDR construction (de Kruif et al., *J. Mol. Biol.* 248:97–105 (1995)), require the construction of large libraries that are technically difficult to make and are hard to handle. The trend in antibody affinity maturation has been towards the isolation of high affinity binders from relatively smaller sized libraries (Pini et al., *J. Biol. Chem.* 273:21769–21776 (1998); Wu et al., *Proc. Natl. Acad. Sci. USA* 95:6037–6042 (1998); Chowdhury et al., *Nature Biotechnol.* 17:568–572 (1999)). All of these approaches involve the construction of expression libraries of antibodies with mutations in the CDRs and selection for better binders.

Phage display technology has become a useful tool for screening large peptide or protein libraries (Winter et al., *Annu. Rev. Immunol.* 12:433–455 (1994); McCafferty, J., *Nature* 348:552–554 (1990); Barbas et al., *Proc. Natl. Acad. Sci. USA* 88:7978–7982 (1991)). Single chain Fvs can be expressed on phage particles as fusions with M13 gene 3 protein in a phagemid vector. The fusion proteins are expressed in *E. coli* and, in the presence of helper phage, are displayed on the tips of M13 phage which can be collected from culture media. Phage that display scFv fusion proteins, which bind to specific antigen, are selected by panning the phage libraries on cells expressing the antigen or on a surface to which the antigen is coupled, such as magnetic beads. Phage which do not bind are washed away, bound phage are eluted and amplified by re-infecting *E. coli*. Several rounds of panning result in an enrichment of specific binders. By making the panning conditions more stringent, better binders can be more effectively separated from poor binders.

Phage display technology can be exploited to develop antibodies which bind to EGFRvIII with higher affinity than MR1. As is well known in the art, an intact antibody comprises two heavy chains and two light chains; each chain has three CDRs, designated 1, 2, and 3, respectively. Each CDR is known to contribute to antigen binding, but they do so unequally. See generally, Kuby, J., *Immunology*, W.H. Freeman & Co., New York (3$^{rd}$ Ed. 1998). While the amino acids of any of the CDRs can be mutated to find mutations which increase affinity, on average, the CDR3 of each chain makes a greater contribution to antigen binding than does the CDR 1 or CDR2 of that chain. See generally, Kuby, supra, at page 117. Thus, mutations of the CDR3 $V_H$ and $V_L$ chains can be particularly advantageous. Moreover, the CDR3 $V_H$ of MR1 is relatively long for a mouse CDR3, which may contribute in part to the relative stability of MR1 scFv relative to other scFvs.

After excluding the last two amino acids of the $V_H$ CDR3 as unlikely to contribute to antigen binding for the reasons discussed in the Introduction, the remaining nine residues in $V_H$ CDR3 was substituted with each of the other 19 natural amino acids. Only mutations of the serine and threonine at amino acid positions 98 and 99, respectively, resulted in improved cytotoxicity of the resulting immunotoxin (the amino acids sequence of the $V_H$ and the $V_L$ CDR3s are set forth in single letter code in Table 5, 6, and 7, infra. The sequence setting forth the $V_H$ does not show the two residues, D101 and Y102, which were considered not likely to contribute to antigen binding.) The preferred substitutions in $V_H$ CDR3 were P98-Y99, which gave an $IC_{50}$ in a PE38 immunotoxin of 3.5 ng/ml, P98-N99, P98-W99, and P98-I99, all of which had $IC_{50}$s of 4.5 ng, P98-F99, with an $IC_{50}$ of 6 ng, and P98-V99, which had an $IC_{50}$ of 6.5 ng. Four clones, P98-S99, W98-V99, S98-W99, and P98-T99, had $IC_{50}$s equal to the parental clone. (By convention, a term such as "P98-Y99" denotes that the amino acid proline appears at position 98 of the designated polypeptide, in this case MR1 $V_H$ CDR3, and that tyrosine appears at position 99, but that the rest of the molecule is that of the normal polypeptide, in this case, the parental antibody MR1.)

With respect to the mutation of the $V_L$ CDR3, only one mutation, F92W, gave an immunotoxin more active than the parent. Its $IC_{50}$ was 1.3 ng/ml. In this case, the "parent" molecule was MR1 with the substitutions P98-Y99 in the VH CDR3, which without the added substitution in the $V_L$ CDR3 had an $IC_{50}$ of 3.5 ng/ml. This mutated MR1, which combined mutations in the CDR3 of both the $V_H$ and the $V_L$ chains ($V_H$ S98P-T99Y-$V_L$F92W), was the most cytotoxic form tested when employed as the targeting portion of an immunotoxin, and is now termed "MR1-1."

These results show that mutations in various CDRs can have an additive effect and can increase the cytotoxicity of the resulting immunotoxin. In view of these results, mutations of the amino acids in the hot spots of CDRs 1 and 2 of the $V_H$ and $V_L$ chains of MR1 will likewise result in antibodies with further improved affinity for EGFRvIII and in immunotoxins with further improved cytotoxicity when compared to MR1.

The best time to analyze clones is early in the process. Panning after the enrichment peaks can be deleterious because of the risk of losing clones. It is possible that Fvs with low affinities but high expression may be preferentially enriched while good binders may be lost. Evidence supporting this was observed while panning the light chain CDR3 libraries: mutant F92S with a low affinity ($K_d$ 22 nM) was found in 7 of 10 clones examined after the third round, whereas, the best binder, F92W, was present only once. In contrast, in the second round F92S was only found in 2 of 17 clones, whereas F92W was present in 6 of 17 clones.

IV. Anti-EGFRvIII Antibodies

The present invention provides antibodies which bind to EGFRvIII with higher affinity than prior art antibodies and which selectively react with EGFRvIII. In particular, the invention provides antibodies which have a lower Kd with regard to EGFRvIII than does MR1, the best previously known scFv targeted to this antigen. Moreover, these antibodies form immunotoxins which have higher cytotoxicity for EGFRvIII-expressing cells than does the same immunotoxin made with MR1. The invention further provides a method for generating antibodies with higher affinity and greater cytotoxicity against EGFRvIII than MR1 has. The immunoconjugates disclosed below target EGFRvIII using antibodies of the present invention. These antibodies are selectively reactive under immunological conditions to those determinants of EGFRvIII displayed on the surface of mammalian cells and accessible to the antibody from the extracellular milieu.

In preferred embodiments of the present invention, the anti-EGFRvIII antibody is a recombinant antibody such as a scFv or a disulfide stabilized Fv antibody. Fv antibodies are typically about 25 kDa and contain a complete antigen-binding site with 3 CDRs on both the heavy and light chains. If the $V_H$ and the $V_L$ chain are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Disulfide stabilized Fvs are taught, for example, in U.S. Pat. No. 5,747,654.

In a particularly preferred embodiment, the antibody is a single chain Fv (scFv). The $V_H$ and the $V_L$ regions of a scFv antibody comprise a single chain which is folded to create an antigen binding site similar to that found in two chain antibodies. Once folded, noncovalent interactions stabilize the single chain antibody. In a more preferred embodiment, the scFv is recombinantly produced. One of skill will realize that conservative variants of the antibodies of the instant invention can be made. Such conservative variants employed in scFv fragments will retain critical amino acid residues necessary for correct folding and stabilizing between the $V_H$ and the $V_L$ regions.

In some embodiments of the present invention, the scFv antibody is directly linked to the effector molecule (EM) through the light chain. However, scFv antibodies can be linked to the EM via its amino or carboxyl terminus.

While the $V_H$ and $V_L$ regions of some antibody embodiments can be directly joined together, one of skill will appreciate that the regions may be separated by a peptide linker consisting of one or more amino acids. Peptide linkers and their use are well-known in the art. See, e.g., Huston et al., *Proc. Nat'l. Acad. Sci. USA* 8:5879 (1988); Bird et al., *Science* 242:4236 (1988); Glockshuber et al., *Biochemistry* 29:1362 (1990); U.S. Pat. No. 4,946,778, U.S. Pat. No. 5,132,405 and Stemmer et al., *Biotechniques* 14:256–265 (1993), all incorporated herein by reference. Generally the peptide linker will have no specific biological activity other than to join the regions or to preserve some minimum distance or other spatial relationship between the $V_H$ and $V_L$. However, the constituent amino acids of the peptide linker may be selected to influence some property of the molecule such as the folding, net charge, or hydrophobicity. Single chain Fv (scFv) antibodies optionally include a peptide linker of no more than 50 amino acids, generally no more than 40 amino acids, preferably no more than 30 amino acids, and more preferably no more than 20 amino acids in length. In some embodiments, the peptide linker is a concatamer of the sequence Gly-Gly-Gly-Gly-Ser (SEQ ID NO:12), preferably 2, 3, 4, 5, or 6 such sequences. However, it is to be appreciated that some amino acid substitutions within the linker can be made. For example, a valine can be substituted for a glycine.

A. Production of scFvs

As described above, in preferred embodiments, the antibody (for example, the targeting moiety of an immunotoxin) is a scFv. Methods of making scFv antibodies have been described. See, Huse et al., supra; Ward et al. *Nature* 341:544–546 (1989); and Vaughan et al., supra. In brief, mRNA from B-cells is isolated and cDNA is prepared. The cDNA is amplified by well known techniques, such as PCR, with primers specific for the variable regions of heavy and light chains of immunoglobulins. The PCR products are purified by, for example, agarose gel electrophoresis, and the nucleic acid sequences are joined. If a linker peptide is desired, nucleic acid sequences that encode the peptide are inserted between the heavy and light chain nucleic acid sequences. The sequences can be joined by techniques known in the art, such as blunt end ligation, insertion of restriction sites at the ends of the PCR products or by splicing by overlap extension (Chowdhury et al., *Mol. Immunol* 34:9 (1997)). After amplification, the nucleic acid which encodes the scFv is inserted into a vector, again by techniques well known in the art. Preferably, the vector is capable of replicating in prokaryotes and of being expressed in both eukaryotes and prokaryotes. In a preferred embodiment, the scFv genes are joined with the PE38 gene by a short linker and cloned into a T7-based expression vector. In particularly preferred embodiments, the scFv is expressed under control of the T7 promoter in *E. coli* BL21 (λ DE3).

As noted in preceding sections, scFv that specifically bind to EGFRvIII are found by panning. Panning can be performed by any of several methods. In a preferred method with respect to the present invention, panning can conveniently be performed using cells expressing EGFRvIII on their surface. A protocol for performing panning using cells is set forth in the Examples, below. Panning can also be performed on a solid surface by coating the solid surface with EGFRvIII and incubating the phage on the surface for a suitable time under suitable conditions. Conveniently, the surface can be a magnetic bead. The unbound phage are washed off the solid surface and the bound phage are eluted.

Finding the antibody with the highest affinity is dictated by the efficiency of the selection process and depends on the number of clones that can be screened and the stringency with which it is done. Typically, higher stringency corresponds to more selective panning. If the conditions are too stringent, however, the phage will not bind. After one round of panning, the phage that bind to EGFRvIII coated plates or to cells expressing EGFRvIII on their surface are expanded in *E. coli* and subjected to another round of panning. In this way, an enrichment of many fold occurs in 3 rounds of panning. Thus, even when enrichment in each round is low, multiple rounds of panning will lead to the isolation of rare phage and the genetic material contained within which encodes the scFv with the highest affinity or one which is better expressed on phage.

Regardless of the method of panning chosen, the physical link between genotype and phenotype provided by phage display makes it possible to test every member of a cDNA library for binding to antigen, even with large libraries of clones.

B. Binding Affinity of Antibodies

The antibodies of this invention bind to an epitope of EGFRvIII with a Kd at least 1 nM lower than that of parental antibody MR1. Binding affinity for a target antigen is typically measured or determined by standard antibody-antigen assays, such as competitive assays, saturation assays, or immunoassays such as ELISA or RIA.

Such assays can be used to determine the dissociation constant of the antibody. The phrase "dissociation constant" refers to a measure of the affinity of an antibody for an antigen. Specificity of binding between an antibody and an antigen exists if the dissociation constant (Kd=1/K, where K is the affinity constant) of the antibody is in the micromolar range, preferably <100 nM, and most preferably <0.1 nM. Antibody molecules will typically have a Kd in the lower ranges. Kd=[Ab-Ag]/[Ab][Ag] where [Ab] is the concentration at equilibrium of the antibody, [Ag] is the concentration at equilibrium of the antigen and [Ab-Ag] is the concentration at equilibrium of the antibody-antigen complex. Typically, the binding interactions between antigen and antibody include reversible noncovalent associations such as electrostatic attraction, Van der Waals forces and hydrogen bonds. This method of defining binding specificity applies to single heavy and/or light chains, CDRs, fusion proteins or fragments of heavy and/or light chains, that are specific for EGFRvIII.

C. Immunoassays

The antibodies can be detected and/or quantified using any of a number of well recognized immunological binding assays (see, e.g., U.S. Pat. Nos. 4,366,241; 4,376,110; 4,517,288; and 4,837,168). For a review of the general immunoassays, see also METHODS IN CELL BIOLOGY, VOL. 37, Asai, ed. Academic Press, Inc. New York (1993); BASIC AND CLINICAL IMMUNOLOGY 7TH EDITION, Stites & Terr, eds. (1991). Immunological binding assays (or immunoassays) typically utilize a ligand (e.g., EGFRvIII) to specifically bind to and often immobilize an antibody. The antibodies employed in immunoassays of the present invention are discussed in greater detail supra.

Immunoassays also often utilize a labeling agent to specifically bind to and label the binding complex formed by the ligand and the antibody. The labeling agent may itself be one of the moieties comprising the antibody/analyte complex, i.e., the anti-EGFRvIII antibody. Alternatively, the labeling agent may be a third moiety, such as another antibody, that specifically binds to the antibody/EGFRvIII protein complex.

In one aspect, a competitive assay is contemplated wherein the labeling agent is a second anti-EGFRvIII antibody bearing a label. The two antibodies then compete for binding to the immobilized EGFRvIII. In embodiments where the question to be answered is to compare the affinity of the first antibody to that of MR1, the second antibody can be MR1. Alternatively, in a non-competitive format, the EGFRvIII antibody lacks a label, but a second antibody specific to antibodies of the species from which the anti-EGFRvIII antibody is derived, e.g., murine, and which binds the anti-EGFRvIII antibody, is labeled.

Other proteins capable of specifically binding immunoglobulin constant regions, such as Protein A or Protein G may also be used as the label agent. These proteins are normal constituents of the cell walls of staphylococcal bacteria. They exhibit a strong non-immunogenic reactivity with immunoglobulin constant regions from a variety of species (see generally, Kronval et al., *J. Immunol.* 111: 1401–1406 (1973); and Akerstrom et al., *J. Immunol.* 135: 2589–2542 (1985)).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antibody, volume of solution, concentrations, and the like. Usually, the assays will be carried out at ambient temperature, although they can be conducted over a range of temperatures, such as 4° C. to 40° C.

While the details of the immunoassays of the present invention may vary with the particular format employed, the method of detecting anti-EGFRvIII antibodies in a sample containing the antibodies generally comprises the steps of contacting the sample with an antibody which specifically reacts, under immunologically reactive conditions, to the EGFRvIII/antibody complex.

V. Production of Immunoconjugates

The anti-EGFRvIII antibodies generated in the present invention can be linked to effector molecules (EM) through the EM carboxyl terminus, the EM amino terminus, through an interior amino acid residue of the EM such as cysteine, or any combination thereof. Similarly, the EM can be linked directly to the heavy, light, Fc (constant region) or framework regions of the antibody. Linkage can occur through the antibody's amino or carboxyl termini, or through an interior amino acid residue. If PE or a cytotoxic fragment thereof is used as the EM, linkages at or near the carboxyl terminus should be made in a manner to maintain, or to add (if the linkage is at the C-terminus) a sequence which functions as a signal sequence to direct the molecule into the cytosol. Appropriate signal amino acid sequences such as REDLK (SEQ ID NO:13) (the sequence of native PE, in single letter code), KDEL (SEQ ID NO:14), RDEL (SEQ ID NO:15), and repeats of KDEL (SEQ ID NO:16), are known in the art. See, e.g., WO 91/18099. Further, multiple EM molecules (e.g., any one of from 2–10) can be linked to the anti-EGFRvIII antibody and/or multiple antibodies (e.g., any one of from 2–5) can be linked to an EM. In a particularly preferred embodiment, KDEL (SEQ ID NO:16) is the C-terminal sequence. The molecule formed by the linking of an effector molecule to an antibody is known as an immunoconjugate.

A therapeutic agent is an agent with a particular biological activity directed against a particular target molecule or a cell bearing a target molecule. One of skill in the art will appreciate that therapeutic agents may include various drugs such as vinblastine, daunomycin and the like, cytotoxins such as native or modified *Pseudomonas* exotoxin or *Diphtheria* toxin, encapsulating agents, (e.g., liposomes) which themselves contain pharmacological compositions, radioactive agents such as $^{125}I$, $^{32}P$, $^{14}C$, $^{3}H$ and $^{35}S$ and other labels, target moieties and ligands.

The choice of a particular therapeutic agent depends on the particular target molecule or cell and the biological effect is desired to evoke. Thus, for example, the therapeutic agent may be a cytotoxin which is used to bring about the death of a particular target cell. Conversely, where it is merely desired to invoke a non-lethal biological response, the therapeutic agent may be conjugated to a non-lethal pharmacological agent or a liposome containing a non-lethal pharmacological agent.

With the therapeutic agents and antibodies herein provided, one of skill can readily construct a variety of clones containing functionally equivalent nucleic acids, such as nucleic acids which differ in sequence but which encode the same EM or antibody sequence. Thus, the present invention provides nucleic acids encoding antibodies and conjugates and fusion proteins thereof.

A. Recombinant Methods

The nucleic acid sequences of the present invention can be prepared by any suitable method including, for example, cloning of appropriate sequences or by direct chemical synthesis by methods such as the phosphotriester method of Narang et al., *Meth. Enzymol.* 68:90–99 (1979); the phosphodiester method of Brown et al., *Meth. Enzymol.* 68:109–151 (1979); the diethylphosphoramidite method of Beaucage et al., *Tetra. Lett.* 22:1859–1862 (1981); the solid phase phosphoramidite triester method described by Beaucage & Caruthers, Tetra. Letts. 22(20):1859–1862 (1981), e.g., using an automated synthesizer as described in, for example, Needham-VanDevanter et al. Nucl. Acids Res. 12:6159–6168 (1984); and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In a preferred embodiment, the nucleic acid sequences of this invention are prepared by cloning techniques. Examples of appropriate cloning and sequencing techniques, and instructions sufficient to direct persons of skill through many cloning exercises are found in Sambrook et al., MOLECULAR CLONING: A LABORATORY MANUAL (2ND ED.), Vols. 1–3, Cold Spring Harbor Laboratory (1989)), Berger and Kimmel (eds.), GUIDE TO MOLECULAR CLONING TECHNIQUES, Academic Press, Inc., San Diego Calif. (1987)), or Ausubel et al. (eds.), CURRENT PROTOCOLS IN MOLECULAR BIOLOGY, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen (San Diego, Calif.), and PE Applied Biosystems (Foster City, Calif.), as well as many other commercial sources known to one of skill.

Nucleic acids encoding native effector molecules (EM) or anti-EGFRvIII antibodies can be modified to form the EM, antibodies, or immunoconjugates of the present invention. Modification by site-directed mutagenesis is well known in the art. Nucleic acids encoding EM or anti-EGFRvIII antibodies can be amplified by in vitro methods. Amplification methods include the polymerase chain reaction (PCR), the ligase chain reaction (LCR), the transcription-based amplification system (TAS), and the self-sustained sequence replication system (3SR). A wide variety of cloning methods, host cells, and in vitro amplification methodologies are well known to persons of skill.

In a preferred embodiment, immunoconjugates are prepared by inserting the cDNA which encodes an anti-EGFRvIII scFv antibody into a vector which comprises the cDNA encoding the EM. The insertion is made so that the scFv and the EM are read in frame, that is in one continuous polypeptide which contains a functional Fv region and a functional EM region. In a particularly preferred embodiment, cDNA encoding a Diphtheria toxin fragment is ligated to a scFv so that the toxin is located at the amino terminus of the scFv. In a most preferred embodiment, cDNA encoding PE or a cytotoxic fragment thereof is ligated to a scFv so that the toxin is located at the carboxyl terminus of the scFv. In the most preferred embodiment, the cytotoxic fragment is PE38.

Once the nucleic acids encoding an EM, an anti-EGFRvIII antibody, or an immunoconjugate of the present invention are isolated and cloned, one may express the desired protein in a recombinantly engineered cell such as bacteria, plant, yeast, insect and mammalian cells. It is expected that those of skill in the art are knowledgeable in the numerous expression systems available for expression of proteins including E. coli, other bacterial hosts, yeast, and various higher eucaryotic cells such as the COS, CHO, HeLa and myeloma cell lines. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain transcription and translation terminators, initiation sequences, and promoters useful for regulation of the expression of the DNA encoding the protein. Conveniently, the cassettes can be placed in plasmids which also contain one or more antibiotic resistance genes. To obtain high level expression of a cloned gene, it is desirable to construct expression cassettes which contain, at the minimum, a strong promoter to direct transcription, a ribosome binding site for translational initiation, and a transcription/translation terminator. For E. coli this includes a promoter such as the T7, trp, lac, or lambda promoters, a ribosome binding site and preferably a transcription termination signal. For eukaryotic cells, the control sequences can include a promoter and preferably an enhancer derived from immunoglobulin genes, SV40, cytomegalovirus, and a polyadenylation sequence, and may include splice donor and acceptor sequences. The cassettes of the invention can be transferred into the chosen host cell by well-known methods such as calcium chloride transformation or electroporation for E. coli and calcium phosphate treatment, electroporation or lipofection for mammalian cells. Cells transformed by the cassettes can be selected by resistance to antibiotics conferred by resistance genes contained in the cassettes, such as the amp, kan, gpt, neo and hyg genes. Kanomycin resistance and ampicillin resistance are preferred embodiments for working with phage.

One of skill would recognize that modifications can be made to a nucleic acid encoding a polypeptide of the present invention (i.e., anti-EGFRvIII antibody, PE, or an immunoconjugate formed from their combination) without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

In addition to recombinant methods, the immunoconjugates, EM, and antibodies of the present invention can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY, VOL. 2: SPECIAL METHODS IN PEPTIDE SYNTHESIS, PART A. pp. 3–284; Merrifield et al. J. Am. Chem. Soc. 85:2149–2156 (1963), and Stewart et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N,N'-dicyclohexylcarbodiimide) are known to those of skill.

B. Purification

Once expressed, the recombinant immunoconjugates, antibodies, and/or effector molecules of the present invention can be purified according to standard procedures of the art, including ammonium sulfate precipitation, affinity columns, ion exchange and gel filtration columns and batch chromatography, and the like (see, generally, R. Scopes, PROTEIN PURIFICATION, Springer-Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as E. coli have been described and are well-known and are applicable to the antibodies of this invention. See, Buchner et al., Anal. Biochem. 205:263–270 (1992); Pluckthun, Biotechnology 9:545 (1991); Huse et al., Science 246:1275 (1989) and Ward et al., Nature 341:544 (1989), all incorporated by reference herein.

Often, functional heterologous proteins from E. coli or other bacteria are isolated from inclusion bodies and require solubilization using strong denaturants, and subsequent refolding. During the solubilization step, as is well-known in the art, a reducing agent must be present to reduce disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., Biochemistry 9: 5015–5021 (1970), incorporated by reference herein, and especially described by Buchner et al., supra.

Renaturation is typically accomplished by dilution (e.g., 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. A preferred yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

VI. Pseudomonas Exotoxin and Other Toxins

Toxins can be employed with antibodies of the present invention to yield immunotoxins. Exemplary toxins include ricin, abrin, diphtheria toxin and subunits thereof, as well as botulinum toxins A through F. These toxins are readily available from commercial sources (e.g., Sigma Chemical Company, St. Louis, Mo.). Diphtheria toxin is isolated from Corynebacterium diphtheriae. Ricin is the lectin RCA60 from Ricinus communis (Castor bean). The term also references toxic variants thereof. For example, see, U.S. Pat. Nos. 5,079,163 and 4,689,401. Ricinus communis agglutinin (RCA) occurs in two forms designated $RCA_{60}$ and $RCA_{120}$ according to their molecular weights of approximately 65 and 120 kD, respectively (Nicholson & Blaustein, J. Biochim. Biophys. Acta 266:543 (1972)). The A chain is responsible for inactivating protein synthesis and killing cells. The B chain binds ricin to cell-surface galactose residues and facilitates transport of the A chain into the cytosol (Olsnes et al., Nature 249:627–631 (1974) and U.S. Pat. No. 3,060,165).

Abrin includes toxic lectins from Abrus precatorius. The toxic principles, abrin a, b, c, and d, have a molecular weight of from about 63 and 67 kD and are composed of two disulfide-linked polypeptide chains A and B. The A chain inhibits protein synthesis; the B-chain (abrin-b) binds to D-galactose residues (see, Funatsu et al., Agr. Biol. Chem. 52:1095 (1988); and Olsnes, Methods Enzymol. 50:330–335 (1978)).

In preferred embodiments of the present invention, the toxin is a Pseudomonas exotoxin A (PE). Native PE is an extremely active monomeric protein (molecular weight 66 kD), secreted by Pseudomonas aeruginosa, which inhibits protein synthesis in eukaryotic cells. The native PE sequence is provided in U.S. Pat. No. 5,602,095, incorporated herein by reference. The method of action is inactivation of elongation factor 2 (EF-2) by ADP-ribosylation. The exotoxin contains three structural domains that act in concert to cause cytotoxicity. Domain Ia (amino acids 1–252) mediates cell binding. Domain II (amino acids 253–364) is responsible for translocation into the cytosol and domain III (amino acids 400–613) mediates ADP ribosylation of elongation factor 2. The function of domain Ib (amino acids 365–399) remains undefined, although a large part of it, amino acids 365–380, can be deleted without loss of cytotoxicity.

The term "Pseudomonas exotoxin" as used herein refers to the native sequence, cytotoxic fragments of the native sequence, and conservatively modified variants of native PE and its cytotoxic fragments. In preferred embodiments, the PE molecule has been modified to delete domain Ia, to reduce or eliminate non-specific binding of the toxin. Cytotoxic fragments of PE include those which are cytotoxic with or without subsequent proteolytic or other processing in the target cell (e.g., as a protein or pre-protein). Cytotoxic fragments of PE include PE40, PE38, and PE35. PE40 is a truncated derivative of PE as previously described in the art. See, Pai et al., Proc. Nat'l Acad. Sci. USA 88:3358–62 (1991); and Kondo et al., J. Biol. Chem. 263:9470–9475 (1988). PE35 is a 35 kD carboxyl-terminal fragment of PE composed of a met at position 280 followed by amino acids 281–364 and 381–613 of native PE. PE38 is a truncated PE pro-protein composed of amino acids 253–364 and 381–613 of PE. PE38 is activated to its cytotoxic form upon processing within a cell (see U.S. Pat. No. 5,608,039, incorporated herein by reference).

In particularly preferred embodiments, PE38 is the toxic moiety of the immunotoxin of this invention. The cytotoxic fragments PE35 and PE40, however, can also be used; these fragments are disclosed in U.S. Pat. Nos. 5,602,095 and 4,892,827, each of which is incorporated herein by reference. Based on work performed with MR1-based immunotoxins, KDEL is a preferred modification of the C-terminal sequence (see Lorimer et al., Proc Natl Acad Sci USA 93:14815–14820 at 14818 (1996).

A. Conservatively Modified Variants of PE

Conservatively modified variants of PE or cytotoxic fragments thereof have at least 80% sequence similarity, preferably at least 85% sequence similarity, more preferably at least 90% sequence similarity, and most preferably at least 95% sequence similarity at the amino acid level, with the PE of interest, such as PE38.

The term "conservatively modified variants" applies to both amino acid and nucleic acid sequences. With respect to particular nucleic acid sequences, conservatively modified variants refer to those nucleic acid sequences which encode identical or essentially identical amino acid sequences, or if the nucleic acid does not encode an amino acid sequence, to essentially identical nucleic acid sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and UGG, which is the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

B. Assaying for Cytotoxicity of PE

*Pseudomonas* exotoxins employed in the invention can be assayed for the desired level of cytotoxicity by assays well known to those of skill in the art. For example, cytotoxicity is often measured using inhibition by *Pseudomonas* exotoxin of protein synthesis as a surrogate measure. See, e.g., Lorimer et al., *Proc. Natl. Acad. Sci. USA* 93:14815–14820 (1996) at 14818. Conveniently, this can be done by measuring the uptake of a radiolabeled amino acid (as taught in Prior et al., *Cell* 64: 1017–1023 (1991)) by cells which do not normally express EGFRvIII but which have been transfected with EGFRvIII cDNA. In the Examples below, uptake of tritiated leucine was measured in NR6M cells (Swiss 3T3 cells selected for lack of expression of mouse EGFR and transfected with human EGFRvIII cDNA). Thus, cytotoxic fragments of PE and conservatively modified variants of such fragments can be readily assayed for cytotoxicity.

A large number of candidate PE molecules can be assayed simultaneously for cytotoxicity by methods well known in the art. For example, subgroups of the candidate molecules can be assayed for cytotoxicity. Positively reacting subgroups of the candidate molecules can be continually subdivided and reassayed until the desired cytotoxic fragment(s) is identified. Such methods allow rapid screening of large numbers of cytotoxic fragments or conservative variants of PE.

C. Other Therapeutic Moieties

Antibodies of the present invention can also be used to target any number of different diagnostic or therapeutic compounds to cells expressing EGFRvIII on their surface. Thus, an antibody of the present invention, such as an anti-EGFRvIII scFv, may be attached directly or via a linker to a drug that is to be delivered directly to cells bearing EGFRvIII. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an anti-EGFRvIII antibody may be an encapsulation system, such as a liposome or micelle that contains a therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735; and Connor et al., *Pharm. Ther.* 28:341–365 (1985).

D. Detectable Labels

Antibodies of the present invention may optionally be covalently or non-covalently linked to a detectable label. Detectable labels suitable for such use include any composition detectable by spectroscopic, photochemical, biochemical, immunochemical, electrical, optical or chemical means. Useful labels in the present invention include magnetic beads (e.g. DYNABEADS®), fluorescent dyes (e.g., fluorescein isothiocyanate, Texas red, rhodamine, green fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase, luciferase, and others commonly used in an ELISA), and colorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

E. Conjugation to the Antibody

In a non-recombinant embodiment of the invention, effector molecules, e.g., therapeutic, diagnostic, or detection moieties, are linked to the anti-EGFRvIII antibodies of the present invention using any number of means known to those of skill in the art. Both covalent and noncovalent attachment means may be used with anti-EGFRvIII antibodies of the present invention.

The procedure for attaching an effector molecule to an antibody will vary according to the chemical structure of the EM. Polypeptides typically contain variety of functional groups; e.g., carboxylic acid (COOH), free amine ($-NH_2$) or sulfhydryl ($-SH$) groups, which are available for reaction with a suitable functional group on an antibody to result in the binding of the effector molecule.

Alternatively, the antibody is derivatized to expose or attach additional reactive functional groups. The derivatization may involve attachment of any of a number of linker molecules such as those available from Pierce Chemical Company, Rockford Ill.

A "linker", as used herein, is a molecule that is used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages which are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

VII. Pharmaceutical Compositions and Administration

The antibody and/or immunoconjugate compositions of this invention (i.e., PE linked to an antibody with a Kd for an epitope of EGFRvIII at least 1 nM lower than that of MR1), are useful for administration into the brain. Use of immunotoxins for brain tumor therapy was recently reviewed by Oldfield, E., and Youle, R., *Curr. Top. Microbiol. Immunol.* 234:97–114 (1998). Small polypeptides cross the blood brain barrier. For longer polypeptides that do not the cross blood brain barrier, methods of administering proteins to the brain are well known. For example, proteins, polypeptides, other compounds and cells can be delivered to the mammalian brain via intracerebroventricular (ICV) injection or via a cannula (see, e.g., Motta & Martini, *Proc. Soc. Exp. Biol. Med.* 168:62–64 (1981); Peterson et al., *Biochem. Pharamacol.* 31:2807–2810 (1982); Rzepczynski et al., *Metab. Brain Dis.* 3:211–216 (1988); Leibowitz et al., *Brain Res. Bull.* 21:905–912 (1988); Sramka et al., *Stereotact. Funct. Neurosurg.* 58:79–83 (1992); Peng et al., *Brain Res.* 632:57–67 (1993); Chem et al., *Exp. Neurol.* 125:72–81 (1994); Nikkhah et al., *Neuroscience* 63:57–72 (1994); Anderson et al., *J. Comp. Neurol.* 357:296–317 (1995); and Brecknell & Fawcett, *Exp. Neurol.* 138:338–344 (1996)).

Thus, for example, glioblastoma may be treated by localized delivery by cannula or by syringe to the tissue surrounding the tumor, or more generally within the central nervous system compartment by ICV. Additionally, the immunoconjugates can be administered systemically where, for example, the patient's glioblastoma has damaged the epithelial cells sufficiently to permit breach of the blood-brain barrier.

The antibody or immunoconjugates of the invention can also be administered locally or systemically for treating breast, ovarian, and lung carcinomas. For example, these malignancies can be treated by direct injection into tumors which cannot be surgically excised. These carcinomas can also be treated by parenteral administration of the immunoconjugates to, for example, locate and kill any metastatic cells which have not yet formed tumors of sufficient size to be treated with radiation or surgery or, indeed, to be readily detected.

The compositions for administration will commonly comprise a solution of the antibody and/or immunoconjugate dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical immunotoxin composition of the present invention for administration to the brain would be about 1.2 to 1200 μg per day. A typical composition for intravenous administration to treat breast, ovarian, or lung carcinoma are about 0.1 to 10 mg per patient per day. Dosages from 0.1 up to about 100 mg per patient per day may be used, particularly if the drug is administered to a secluded site and not into the circulatory or lymph system, such as into a body cavity or into a lumen of an organ. Actual methods for preparing administrable compositions will be known or apparent to those skilled in the art and are described in more detail in such publications as REMINGTON'S PHARMACEUTICAL SCIENCE, 19TH ED., Mack Publishing Company, Easton, Pa. (1995).

The compositions of the present invention can be administered for therapeutic treatments. In therapeutic applications, compositions are administered to a patient suffering from a disease, such as a glioblastoma, breast carcinoma, ovarian carcinoma, or lung carcinoma, in an amount sufficient to at least slow or partially arrest the disease or its complications. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the immunoconjugate compositions of the present invention can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm, so only nanoparticles are administered intravenously. Microparticles are typically around 100 μm in diameter and are administered subcutaneously or intramuscularly. See, e.g., Kreuter, J., COLLOIDAL DRUG DELIVERY SYSTEMS, J. Kreuter, ed., Marcel Dekker, Inc., New York, N.Y., pp. 219–342 (1994); and Tice & Tabibi, TREATISE ON CONTROLLED DRUG DELIVERY, A. Kydonieus, ed., Marcel Dekker, Inc. New York, N.Y., pp. 315–339, (1992) both of which are incorporated herein by reference.

Polymers can be used for ion-controlled release of immunoconjugate compositions of the present invention. Various degradable and nondegradable polymeric matrices for use in controlled drug delivery are known in the art (Langer, R., *Accounts Chem. Res.* 26:537–542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425–434 (1992); and Pee et al., *J. Parent. Sci. Tech.* 44(2):58–65 (1990)). Alternatively, hydroxyapatite has been used as a microcarrier for controlled release of proteins (Ijntema et al., *Int. J. Pharm.* 112:215–224 (1994)). In yet another aspect, liposomes are used for controlled release as well as drug targeting of the lipid-capsulated drug (Betageri et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Among various uses of the immunotoxins of the present invention are included disease conditions caused by specific human cells expressing EGFRvIII that may be eliminated by the toxic action of the immunoconjugate. One preferred application for the immunotoxins of the invention is the treatment of malignant cells expressing EGFRvIII. Exemplary malignant cells include cells of glioblastoma, breast carcinoma, ovarian carcinoma, and lung carcinoma.

VIII. Diagnostic Kits and In Vitro Uses

In another embodiment, this invention provides for kits for the detection of EGFRvIII in a biological sample. A "biological sample" as used herein is a sample of biological tissue or fluid that contains EGFRvIII. Such samples include, but are not limited to, tissue from biopsy, sputum, amniotic fluid, blood, and blood cells (e.g., white cells). Fluid samples may be of some interest, but are generally not preferred herein since detectable concentrations of EGFRvIII are rarely found in such a sample. Biological samples also include sections of tissues, such as frozen sections taken for histological purposes. A biological sample is typically obtained from a multicellular eukaryote, preferably a mammal such as rat, mouse, cow, dog, guinea pig, or rabbit, and more preferably a primate, such as a macaque, chimpanzee. Most preferably, the biological sample is from a human.

Kits will typically comprise an anti-EGFRvIII scFv of the present invention, which has a higher affinity for EGFRvIII than does MR1 scFv.

In addition the kits will typically include instructional materials disclosing means of use of an antibody of the present invention (e.g. for detection of EGFRvIII-containing cells in a sample). The kits may also include additional components to facilitate the particular application for which the kit is designed. Thus, for example, the kit may additionally contain means of detecting the label (e.g. enzyme substrates for enzymatic labels, filter sets to detect fluorescent labels, appropriate secondary labels such as a sheep anti-mouse-HRP, or the like). The kits may additionally include buffers and other reagents routinely used for the practice of a particular method. Such kits and appropriate contents are well known to those of skill in the art.

In one embodiment of the present invention, the diagnostic kit comprises an immunoassay. As described above, although the details of the immunoassays of the present invention may vary with the particular format employed, the method of detecting EGFRvIII in a biological sample generally comprises the steps of contacting the biological sample with an antibody which specifically reacts, under immunologically reactive conditions, to EGFRvIII with higher affinity to EGFRvIII than does MR1 scFv. The antibody is allowed to bind to EGFRvIII under immunologically reactive conditions, and the presence of the bound antibody is detected directly or indirectly.

Due to the increased affinity of antibodies developed by the methods taught herein, and of the scFv designated MR1-1, in particular, the antibodies provided herein will be especially useful as diagnostic agents and in in vitro assays to detect the presence of EGFRvIII in biological samples. For example, MR1-1, and other antibodies made by the methods taught herein, can be used as the targeting moieties of immunoconjugates in immunohistochemical assays to determine whether a sample contains cells expressing EGFRvIII. If the sample is one taken from a tissue of a patient which should not normally express EGFRvIII, detection of EGFRvIII would indicate either that the patient has a cancer characterized by the presence of EGFRvIII-expressing cells, or that a treatment for such a cancer has not yet been successful at eradicating the cancer. Persons of skill in the art will also appreciate that the anti-EGFRvIII antibodies of the invention, coupled to an appropriate label, can likewise be used in vivo to detect the presence of EGFRvIII expressing cells, thereby indicating either that the patient has a cancer characterized by the presence of EGFRvIII-expressing cells, or that a treatment for such a cancer has not yet been successful at eradicating the cancer.

EXAMPLES

Example 1

Strategy to Develop Antibodies with Better Binding than that of MR1.

To discover antibodies with better binding to EGFRvIII than that of MR1, a phage display library was made with MR1 scFv. Random mutations were introduced in heavy chain complementarity determining region 3 ($V_H$CDR3), an area that has a major role in antigen binding (MacCallum et al., *J. Mol. Biol.* 262:732–745 (1996)). Panning on cells expressing EGFRvIII produced several mutants which, when used to construct immunotoxins, had improved affinity, cytotoxicity, and yield. Analysis of these variants revealed that they all had mutations localized to a region of the $V_H$CDR3 which qualifies as a hot spot for hypermutation (Neuberger et al., *Curr Opin. Immunol.* 7:248–254 (1995); Jolly, C. J., *Semin. Immunol.* 8:159–168 (1996); Neuberger et al., *Immunological Rev.* 62:107–116 (1998)). Hot spots are defined by the consensus sequences G/A-G-T/C-A/T or A-G-C/T. The latter contains serine codons found in the variable domain genes of antibodies (Goyenechea et al., *Proc. Natl. Acad. Sci. USA* 93:13979–13984 (1996)). Hot spots are regions that mutate at a high frequency during the maturation of antibodies. Panning the $V_H$CDR3 library did not yield any clones containing mutations outside the hot spots. This result confirms recent findings that randomizing hot spots is more likely to produce mutants with improved affinity (Chowdhury et al., *Nature Biotechnol.* 17:568–572 (1999)). The best binder obtained from panning the $V_H$CDR3 library was used to make a phage display library randomizing a hot spot in the light chain CDR3. Panning this library produced several more mutant clones with even more desirable characteristics.

Example 2

Construction of $V_H$ Mutant Library. The $V_H$CDR3 of MR1 consists of eleven amino acids. As noted in the Introduction, two of these amino acids were considered unlikely to participate in antigen binding. The other nine amino acids in the $V_H$ were mutated by substituting all of the other natural amino acids as follows for the amino acid residue normally occurring at the position. DNA oligomers were designed to generate three libraries, each randomizing nine nucleotides, (three consecutive amino acids). MR1 phagemid was used as template to introduce three amino acid randomizations in the CDR3 heavy chain in 3 separate two-step polymerase chain reactions (PCR) (FIG. 1). The following oligos were used:

CDR3Hb (5'-CTTGGCCCCASNNSNNSNNAGAGGTAC-TAGAATAGCCTCTTGTGCA-3'), (SEQ ID NO: 1)

CDR3Hd (5'-CTTGGCCCCACATAGCATASNNSNNSN-NAGAATAGCCTCTTGTGCA-3'), (SEQ ID NO: 2)

CDR3Hf (5'-CTTGGCCCCACATAGCATAAGAGG-TACTSNNSNNSNNTCTTGTGCA-3'), (SEQ ID NO: 3)

S1 (5'-CAACGTGAAAAAATTATTATTCGC-3'), (SEQ ID NO: 4)

AMBN (5'-GCTAAACAACTTTCAACAGTCTAT-GCGGGCAC-3') (SEQ ID NO: 5).

```
CDR3Hb  (5'-CTTGGCCCCASNNSNNSNNAGAGGTACTAGAATAGCCTC
         TTGTGCA-3'),
         (SEQ ID NO: 1)

CDR3Hd  (5'-CTTGGCCCCACATAGCATASNNSNNSNNAGAATAGCCTC
         TTGTGCA-3'),
         (SEQ ID NO: 2)

CDR3Hf  (5'-CTTGGCCCCACATAGCATAAGAGGTACTSNNSNNSNNTC
         TTGTGCA-3'),
         (SEQ ID NO: 3)

S1      (5'-CAACGTGAAAAAATTATTATTCGC-3'),
         (SEQ ID NO: 4)

AMBN    (5'-GCTAAACAACTTTCAACAGTCTATGCGGGCAC-3')
         (SEQ ID NO: 5)
```

In the first PCR, 50 pg of the phagemid pCANTAB 5 E-MR1 was used as the template in three separate reactions using 20 pmol DNA oligomer S1 along with 20 pmol of the DNA oligomer CDR3Hb, CDR3Hd or CDR3Hf. The template and oligos were mixed with 2 Ready-To-Go PCR Beads (Pharmacia) in a 50 µl volume and then cycled using the following profile: 1 cycle at 95° C. for 5 minutes, followed by 30 cycles of 94° C. for 1 minute, 55° C. for 1 minute, and 72° C. for 1 minute. These reactions generated 407 bp products which contain the mutations. The products generated in the first step were then used as primers in three separate reactions with primer AMBN using the MR1 phagemid as template. In these reactions, 1 µl of the product from the first reaction was used with 20 pmol of the DNA oligomer AMBN with 50 pg phagemid pCANTAB 5 E-MR1 as the template. The primers and template were mixed with 2 PCR Beads in a 50 µl volume and cycled using the profile described above. Each reaction generated a 876 bp library. The PCR products were digested with restriction enzymes Sfi I and Not I and purified. 150 ng of the purified PCR products was ligated with 250 ng of the phage display vector DNA pCANTAB5E (pre-digested as supplied by Pharmacia). The ligation mixtures were desalted, and 40 ng of each ligation was used to transform *E. coli* TG1. Each transformation resulted in approximately $1.5 \times 10^6$ clones. The phage libraries were then rescued from the transformed bacteria. Cells from each transformation were grown in 10 ml 2×YT (16 g bacto-tryptone, 10 g bacto-yeast extract, 5 g NaCl per liter in $H_2O$) containing 2% glucose at 37° C. shaking at 250 RPM. After one hour ampicillin (100 µg/ml final concentration) and $1 \times 10^{10}$ plaque forming units (pfu) of M13KO7 helper phage were added. The cultures were grown for 1 hour, pelleted, then resuspended in 10 ml 2×YT plus ampicillin (100 µg/ml) and kanamycin (50 µg/ml) and grown for 16 hours at 37° C., shaking at 250 RPM. The bacteria were pelleted by centrifugation in a Sorval SS34 rotor at 8000 RPM for 20 minutes. The phage-containing supernatants were filtered using a 0.45 micron syringe filter unit. The phage were then precipitated by adding 2 ml PEG, NaCl (20% PEG8000 in 2.5 M NaCl w/v) then incubated on ice for 30 minutes. The precipitated phage were pelleted by centrifugation in a Sorvall SS34 rotor at 10K RPM for 20 minutes, then resuspended in 1 ml NTE (100 mM NaCl, 10 mM TRIS pH 7.5, 1 mM EDTA). The rescued phage libraries were titered and stored at 4° C.

Panning the $V_H$CDR3 Library. NR6M cells grown in DMEM containing 10% fetal bovine serum plus 750 µg/ml G418 were harvested using 0.02% EDTA (Sigma #E-8008). $2 \times 10^7$ cells were pelleted and resuspended in 10 ml cold blocking buffer (2% BSA, 0.02% $NaN_3$ in DPBS) and rotated slowly for 1 hour at 4° C. The cells were pelleted and resuspended in 5 ml cold blocking buffer. $1 \times 10^9$ phage from each of the heavy chain CDR3 libraries was added to the cell suspension and the mixture was rotated slowly at 4° C. for 2 hours. The cells were washed twice with 10 ml cold blocking buffer and resuspended in 5 ml cold blocking buffer. MR1dsFvPE38 was added (2 µM final concentration) as a competitive inhibitor, and the suspension was rotated slowly at 4° C. for 2 hours. The cells were washed three times with 10 ml cold blocking buffer. Bound phage were eluted by resuspending the washed cells in 1.5 ml ice cold 50 mM HCl, and incubated on ice for 10 minutes. The NR6M cells were pelleted and the eluted phage were transferred to a new tube containing 200 µl 1 M Tris pH 8.0. The eluted phage were titered to determine the number of phage captured. Then 0.5 ml of the eluted phage were amplified by reinfecting *E. coli* TG1 for use in the next round of panning.

Construction of $V_L$ Mutant Library. Heavy chain CDR3 mutant (S98P-T99Y) was used as a template in a two step PCR which introduced randomizations in the hot spot located in the light chain CDR3. In the first reaction, 50 pg of the phagemid containing heavy chain mutant (S98P-

T99Y) was mixed with 20 pmol of the DNA oligomers VLMUT (5'-GATTACTACTGTTTG-CAANNSNNSAACGTGCCTCTTACA-3') (SEQ ID NO: 6) and AMBN in a 50 µl volume. The mixture was cycled using the same profile used to generate the heavy chain CDR3 library. The reactions generated 150 base pair products containing randomization of the "hot spot" in the light chain CDR3. After purification, 1 µl of the reaction product generated in the first PCR was used with 20 pmol DNA oligomer S1 in a second PCR with 50 pg of the phagemid DNA containing the heavy chain mutant (S98P-T99Y) as the template. The template and primers were mixed with 2 PCR Beads in a 50 µl volume and cycled using the above profile. The reactions generated a 876 base pair library which contains the $V_H$CDR3 mutation (S98P-T99Y) and randomization of the hot spot in CDR3L. The PCR products were digested with restriction enzymes Sfi I and Not I, purified and ligated with the pCANTAB5E vector as with the heavy chain CDR3 libraries. The ligation was desalted and one tenth (40 ng) of the reaction was used to transform E. coli TG1. The phage library containing $3 \times 10^5$ clones was rescued as described in the heavy chain CDR3 construction. One quarter of it was amplified and used for the first round of panning.

Panning the $V_L$CDR3 Library. NR6M cells were harvested as in the $V_H$CDR3 panning procedure. All steps and washes were done in cold blocking buffer except as noted. $5 \times 10^6$ cells were resuspended in 1 ml blocking buffer and rotated for 1 hour. The cells were pelleted and resuspended, rescued phage library was added and the suspension was rotated slowly at 4° C. for 2 hours. The cells were washed 3 times then resuspended in blocking buffer containing 2 pM MR1 heavy chain mutant (S98P-T99Y) scFv-PE38 and rotated slowly at 4° C. for 2 hours. The cells were washed 3 times and bound phage were eluted and neutralized as with the heavy chain CDR3 library. The eluted phage were titered and rescued for the next round of panning.

Phage Rescue. The phage captured after each round of panning were amplified for use in the next round of panning. For rescue, E. coli TG1 was grown in 10 ml 2×YT containing 2% glucose incubated at 37° C., 250 RPM. When the $OD_{600}$ reached 0.3, 0.5 ml of the captured phage were added to the culture and the incubation was continued. After one hour ampicillin (100 µg/ml final) and $1 \times 10^{10}$ pfu of M13KO7 helper phage were added and incubation continued for one hour. The culture was then centrifuged and the pelleted bacteria were resuspended in 10 ml fresh 2×YT media containing ampicillin (100 µg/ml) and kanamycin (50 µg/ml) and incubated at 37° C., 250 RPM for 16 hours. The bacteria were pelleted by centrifugation in a Sorvall SS34 rotor at 8K RPM for 20 minutes. The phage containing supernatants were filtered using a 0.45 micron syringe filter unit. The phage were then precipitated by adding 2 ml PEG/NaCl (20% PEG8000 in 2.5 M NaCl w/v) and incubated on ice for 30 minutes. The precipitated phage were pelleted by centrifugation in a Sorvall SS34 rotor at 10K RPM for 20 minutes, then resuspended in 1 ml NTE (100 mM NaCl, 10 mM TRIS, 1 mM EDTA pH 7.4). The rescued phage library was titered and stored at 4° C.

Detection of Positive Clones. After the third round of panning, 48 clones from the heavy chain CDR3 library were analyzed for binding to EGFRvIII peptide (LEEKKGNYV-VTDHSGGK-biotin) (SEQ ID NO: 7) using ELISA. Twenty-two clones which gave the strongest signal were subjected to DNA sequencing and further analyzed. After the fourth round of panning, 48 clones were analyzed by ELISA and the DNA sequence of the 10 clones with the strongest ELISA signal was determined. For the light chain library, after the second round of panning, 48 clones were analyzed by ELISA and 17 with the strongest signal were sequenced. After the third round, 20 clones were analyzed and 10 clones with the highest ELISA signals were subjected to DNA sequencing. To rescue the phage from the individual clones, single colonies were picked from the final panning titer plate and inoculated into 150 µl 2×YT with 2% glucose and 100 xg/ml ampicillin in a 96 well culture dish. The dish was incubated at 37° C., 150 RPM. After 3 hours, 20 µl of the culture was transferred to the wells of a second dish containing 100 µl 2×YT with 2% glucose and 100 µg/ml ampicillin plus $1 \times 10^8$ M13KO7 helper phage and incubated for 2 hours. The cultures were pelleted and resuspended in fresh 2×YT plus ampicillin and kanamycin, then grown 16 hours. The cells were pelleted and 50 to 100 µl of the phage-containing supernatants were assayed in ELISA. Phage ELISA was done as described (Lorimer et al., *Proc. Natl. Acad. Sci. USA* 93:14815–14820 (1996)) except 100 µl 3,3',5,5'-tetramethyl benzidine (BM blue, Boehringer Mannheim) was used as substrate for detection. After blue/green color developed, 100 µl 2 M $H_2SO_4$ was added to stop color development. Absorption was measured at 450 nM.

DNA Sequencing. DNA sequencing was preformed using a PE Applied Biosystems (Foster City, Calif.) Rhodamine Terminator Cycle Sequencing Kit. The samples were run and analyzed on a PE Applied Biosystems Model 310 automated sequencer.

ScFv Immunotoxin Plasmid Construction, Expression and Purification. ScFvs from selected phagemid clones were PCR amplified using primers which introduced NdeI and HindIII restriction sites. The products were then digested and cloned into a T7 based expression vector in which the scFv is fused to a truncated version of *Pseudomonas* exotoxin A. The plasmids were transformed into the expression host BL21 (λDE3). The MR1 mutant immunotoxins were expressed and prepared as described previously (Buchner et al., *Anal. Biochem.* 205:263–270 (1992)).

Surface Plasmon Resonance. Binding kinetics were measured using a BIAcore 2000 Biosensor (Biacore, Inc., Piscataway, N.J.). Steptavidin was bound to a CM5 research grade sensor chip using amine coupling reagents provided by BIAcore. Biotinylated EGFRvIII peptide was bound to the streptavidin by injecting 10 µl of a 10 nM solution of the peptide over the chip. Immunotoxins were diluted to 25 µg/ml in hepes buffered saline (HBS). On and off rates were measured by injecting 50 µl of the diluted immunotoxin over the chip surface at 10 µl/minute then allowing the bound material to disassociate for 5 minutes or more. The remaining bound material was removed from the EGFRvIII peptide by injecting 5 µl of 100 mM phosphoric acid. Binding kinetics were analyzed using BIAevaluation 2.1 Software.

Cell Culture and Cytotoxicity Assays. NR6M cells were cultured in DMEM plus 10% fetal bovine serum supplemented with 750 µg/ml G418. Cytotoxicity assays measured inhibition of [$^3$H]-leucine incorporation as previously described (Prior et al., *Cell* 64:1017–1023, 1991).

Bacteria and Cell Lines. E. coli TG1; K12 Δ (lac-pro), supE, thi, hsd Δ 5/F'[traD36, proAB, lacI$^q$, lacZ Δ M15]. E. coli BL21(λDE3); F$^-$ ompT [lon] hsdS$_B$ ($r_B^-$ $m_B^-$; an E. coli B strain) with DE3, a λ prophage carrying the T7 RNA polymerase gene. NR6 is a Swiss 3T3 mouse fibroblast variant cell line with no detectable EGFR. NR6M is the NR6 cell line transfected with a cDNA for the mutant EGFRvIII receptor under the control of the β-actin promoter. The source of NR6 and NR6M has been previously described (Lorimer et al., *Clin. Cancer Res.* 1: 859–864 (1995)).

Example 3

Construction of the $V_H$CDR3 Library. To increase the affinity of the MR1(Fv) and the activity of the corresponding immunotoxin MR1(FV)-PE38, we mutated $V_H$CDR3 and $V_L$CDR3 because these portions of the antibody make significant contacts with the antigen (MacCallum et al., *J. Mol. Biol.* 262:732–745 (1996)). The first nine of the eleven amino acids of $V_H$CDR3 are shown in Table 5 (the last two, D101 and Y102 are excluded since they were considered unlikely to contribute to antigen binding). Because a complete library in which nine amino acid residues were randomized would require more than $5 \times 10^{11}$ individual clones, we instead prepared three different libraries covering residues 95–97, 98–100 and 101A–101C as described in Example 1. Library H-CDR3 95–97 contained $1.6 \times 10^6$ clones, library H-CDR3 98–100, contained $4 \times 10^5$ clones and library H-CDR3, 100A–100C contained $1 \times 10^6$ clones. To ensure the libraries were properly made, five clones from each library were sequenced. As expected, each clone had different amino acid combinations in the region targeted for mutations. Since a completely diverse library randomizing 3 amino acids would require only $8 \times 10^3$ independent clones, the size of the libraries ensures that all possible DNA sequences are well represented.

Panning of $V_H$CDR$^3$ Library and Analysis of Selected Clones. Because the final intended use for an improved MR1 mutant was to target a toxin to EGFRvIII-positive cancer cells, we used EGFRvIII positive NR6M cells for panning. Panning was done in the presence of immunotoxin MR1 (Fv)-PE38, which was expected to act as a competitor against the selection of wild type MR1 Fv in the library. The phage from each library were rescued and equal amounts of phage ($1 \times 10^9$) from each library were pooled to begin the first round of panning. The eluted phage were titered and rescued for the next round of panning. The subsequent pannings were done without determining the titer of the rescued phage until after the panning was carried out. This was done to save time, and to decrease the possibility that unstable binders might be lost in the 24 hours required to titrate the rescued phage. Typically the rescues yielded $1 \times 10^{12}$ cfu/ml. Table 3 summarizes the number of phage captured during each of the 4 rounds of panning. The enrichment peaked at the third round, and appeared to decrease at the fourth round.

We initially examined the phage selected after four rounds of panning. Forty eight clones were analyzed for binding in a phage ELISA and the DNA sequence of ten of the clones with the strongest signal was determined. As shown in Table 6, the only mutations recovered were in positions 98 and 99. DNA sequence analysis showed that the clones belong to five different groups: parental S98-T99; and mutants P98-N99; P98-Y99; P98-F99 and P98-W99. We also examined phage selected after the 3rd round to see if good binders were lost between round 3 and 4. We analyzed 48 individual clones for binding to the EGFRvIII peptide by ELISA and 22 of these which gave the highest signal were subjected to DNA sequencing. Again, the only mutations recovered were in positions 98 and 99 (Table 6). A variety of amino acids were recovered in these positions. The most frequent was S98-T99 (wild type) followed by P98-S99; P98-Y99; P98-N99 and A98-D99. The fourth round of panning resulted in an enrichment of clones P98-N99 and P98-Y99 over the wild type (S98-T99), a loss of several clones and also produced a new clone containing P98-F99.

Cytotoxicity and Affinity of $V_H$CDR3 Mutants. Each of the 12 mutants that were obtained by panning the MR1 $V_H$CDR3 library were used to make immunotoxin. Each immunotoxin was constructed by PCR amplifying the Fvs from the phage display vector and subcloning them into the immunotoxin expression vector. All of the immunotoxins (except one containing the A98-D99 mutation in $V_H$CDR3) could be highly purified to more than 90–95% homogeneity. The purified immunotoxins were used to determine their cytotoxicity on NR6M cells. The binding affinities were measured by the Biacore method using either peptide immobilized on a chip (or a mutant form of the extracellular domain of the EGFR attached to a chip). The results of one set of experiments is shown in Table 6; compared to the parental clone (S98-T99) which had an $IC_{50}$ of 8.0 ng/ml, there were six clones which were more cytotoxic. These were P98-Y99 which had an $IC_{50}$ of 3.5 ng/ml followed by P98-N99, P98-W99, P98-I99 which had an $IC_{50}$ of 4.5 ng, P98-F99 with an $IC_{50}$ of 6 ng/ml, and P98V99 with an $IC_{50}$ of 6.5 ng/ml. Four clones, P98-S99, W98-F99, S98-W99 and P98-T99 had $IC_{50}$s identical to the parental clone.

Construction of the $V_L$CDR3 Library. All of the mutants recovered after panning the $V_H$CDR3 libraries were localized to positions 98 and 99. The DNA sequence of these two residues constitutes a hot-spot which is a region which undergoes mutations during the in vivo affinity maturation of an antibody. The mutant with the highest cytotoxic activity from the $V_H$ library was used and subjected to mutagenesis targeting only the hot spot in $V_L$CDR3. The sequence of $V_L$CDR3 is shown in Tables 5 and 7. The library introduced randomizations in the hot spot that coded for residues 91 and 92. The $V_L$CDR3 phage library was constructed as described in Example 1, and contained $3 \times 10^5$ clones. Since a library of only 400 clones is required to achieve all possible amino acid combinations in the two positions chosen for mutation, it can be assumed that all possible DNA sequences were abundant in this library.

Panning of $V_L$CDR3 library and analysis of selected clones. Three rounds of panning were carried out and the phage captured at each step is shown in Table 3. For this library we obtained more enrichment in the second round of panning than in the third round. After the second round of panning 48 individual clones were rescued, binding to peptide measured by ELISA, and the DNA sequence of seventeen clones that gave the strongest signal was determined. As shown in Table 7, five different mutants were obtained. All retained the wild type serine residue at position 91 and had mutations at residue 92. The most frequent was F92W (6 of 17), followed by F92R (3 of 17), F92S (2 of 17), F92L (1 of 17) and F92M (1 of 17). Of the 17 analyzed, 4 were found to be the parental type.

The properties of clones isolated after the third round of panning were also analyzed (Table 7). Twenty clones were picked at random, the phage were rescued and checked for binding to peptide by ELISA. Ten clones that gave the strongest signal were chosen for DNA sequence analysis. The DNA sequence revealed that there were 3 different clones present, all which were represented in round 3. Besides one parental clone, these clones were F92S (7 of 10), F92W (1 of 10), and F92R (1 of 10). There were no new mutants found and we did not find mutants F92L and F92M.

Cytotoxicity and Binding Properties of the $V_L$CDR3 Mutants. The different Fvs obtained were used to make immunotoxins and their cytotoxic activities and binding affinities were measured using the purified recombinant proteins. Only one mutant, F92W gave an immunotoxin that was more active than the parent. Its $IC_{50}$ was 1.3 ng/ml compared to 3.5 ng/ml for its parent (Table 7). The other mutants had lower activities. The data in Table 7 also showed that F92W has a higher affinity ($K_d$ 3 nM) than the parental clone F92 ($K_d$ 6 nM). One other mutant, F92L, had a slightly increased affinity ($K_d$ 4 nM), but not an increase in cytotoxicity. FIG. 2 shows a BIACore sensorgram comparing the binding properties of the parental clone with the most active immunotoxin made from the Fv obtained from the $V_H$CDR3 library ($V_H$S98P-T99Y) and the most active clone obtained from the $V_L$CDR3 library ($V_H$S98P-T99Y-$V_L$F92W), which is now called MR1-1. The Figure shows that the two mutants have slower dissociation rates than the parental Fv. The analysis of the immunotoxin (MR1-1-(Fv)-PE38) with both $V_H$ and $V_L$ mutations showed that it had a decrease in $k_{off}$ and a slight increase in $k_{on}$, resulting in a $K_d$ of 3 nM.

Table 4 shows two experiments in which the cytotoxic activities of MR1(Fv)-PE38 was compared with two improved variants: MR1(Fv)(VHS98P-T99Y)-PE38 and MR1-1(Fv)-PE38. In both experiments the MR1(Fv)-PE38 was the least active and MR1-1(Fv)-PE38 was the most active.

Example 4

Immunotoxin Yield. A notable increase in the yield of different mutant immunotoxins was observed during the purification process. After refolding, the proteins are dialyzed and purified by chromatography (Buchner et al., *Anal. Biochem.* 205:263–270 (1992)). The protein is first batch-purified on a Q-Sepharose anion exchange resin which removes gross protein aggregates, nucleic acids and other contaminants. Next the eluted protein is loaded on to a MonoQ column and the proteins are eluted with a 0–0.3M NaCl continuous gradient. This step removes smaller aggregates. The properly folded monomeric immunotoxin elutes from MonoQ at a characteristic NaCl concentration of 280 mM. The purity of the collected MonoQ fractions is confirmed by observing a single monomeric peak eluted from a TSK G3000SW size exclusion column and by SDS-PAGE. The yield of each mutant immunotoxin MR1(Fv)-PE38 is calculated based on the amount of protein collected from the peak MonoQ fractions and the presence of a single peak on the size exclusion chromatogram (TSK 3000). Tables 6 and 7 show the yields when 100 mg of inclusion body protein is subjected to purification. It is evident that the yield of immunotoxin is greatly affected by the mutations in the CDRs and increased from 2% with the parental MR1(Fv)-PE38 to as much as 10–17.5% with many of the mutants.

Example 5

Figure 3:
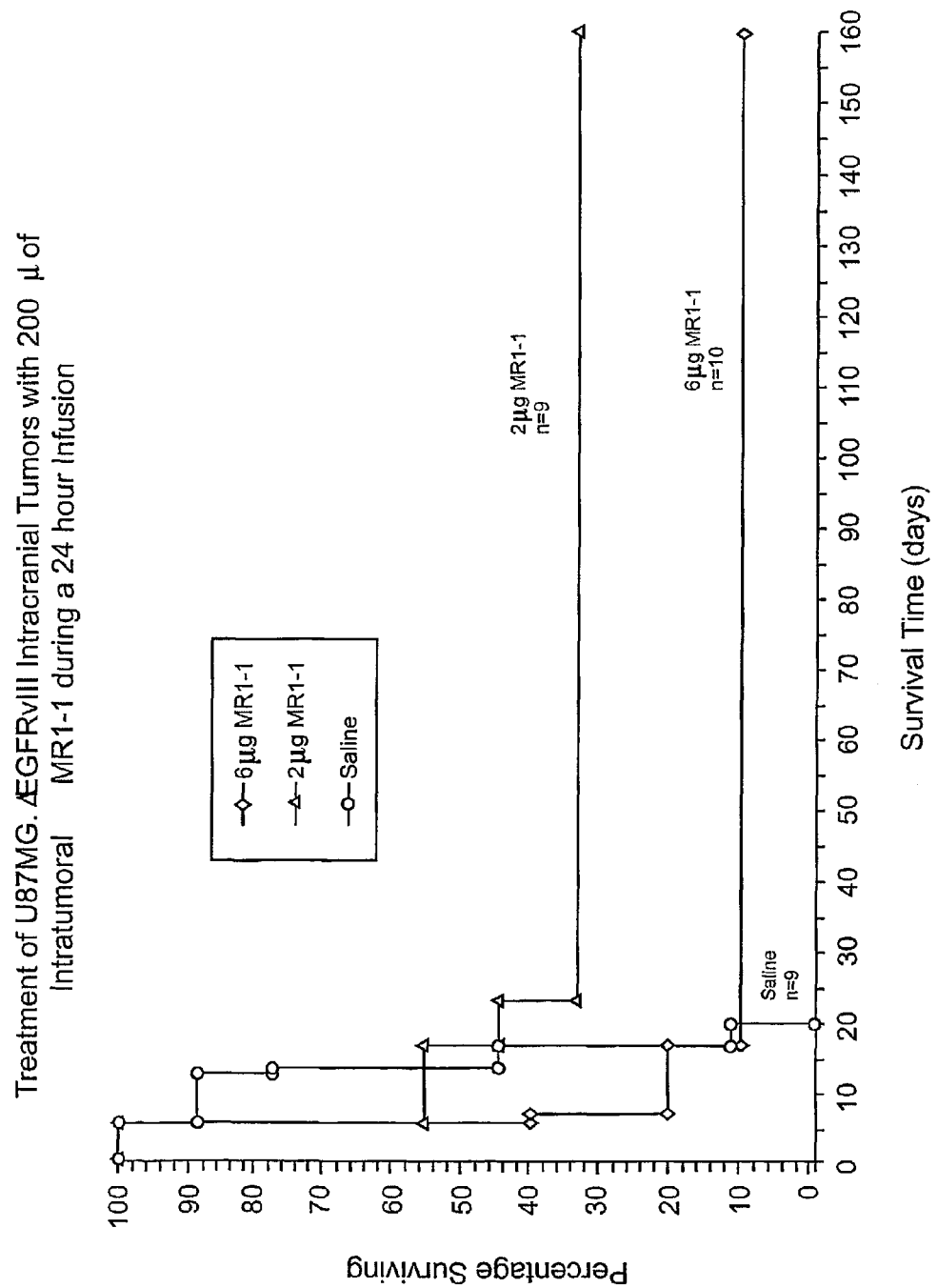
FIG. 3. Survival of athymic rats with intracranial tumors of human glioblastoma cells transfected with EGFRvIII treated with MR1-1-targeted immunotoxin. The Y-axis shows the percentage of animals surviving at a given point in time. The X-axis shows the survival time in days. Legend: MR1-1 denotes MR1-1-PE38 immunotoxin. Filled diamonds, animals administered 6 μg of MR1-1-PE38 immunotoxin over a 7 day period by 24 hour infusion. Open triangle: animals administered 2 μg of MR1-1-PE38 immunotoxin on the same schedule. Open circle: animals administered saline control on the same schedule.

EGFRvIII intracranial tumors were initiated in athymic rats by the injection of $10^5$ U87MG.ΔEGFRvIII cells (a human glioblastoma cell line created by transfecting U87MG cells with EGFRvIII, see, Nishikawa et al., Proc Natl Acad Sci (USA) 91:7727–7730 (1994)) through a catheter placed 1 mm anterior and 4 mm lateral to bregma. Tumors were treated with an infusion of MR1-1-PE38 immunotoxin or saline control through the catheter directly into the tumor. The immunotoxin was administered at doses of either 2 or 6 μg in 200 μl of phosphate buffered saline ("PBS") with 0.2% human serum albumin ("HSA") over a 7 day period, using an Alzet® 2Ml osmotic pump (Durect Corp., Cupertino, Calif.), control animals were administered 200 μl of the PBS-HSA solution. Treatment was initiated 3 days following tumor inoculation. As shown in FIG. 3, all animals receiving the saline control were dead at 20 days. Ten percent of animals receiving the 6 μg dose were still alive at 160 days. Over thirty percent of animals treated with the 2 μg dose were still alive at 160 days. The difference in survival between the 2 μg and the 6 μg doses suggests that in an intracranial setting, the concentration of immunotoxin at the 6 μg dose may have been high enough to cause some non-specific toxicity to the brain tissue which was reduced or not present at the 2 μg dose, but that at both doses, the immunotoxin prolonged survival.

Example 6

EGFRvIII intracranial tumors were initiated in athymic rats by the injection of $10^5$ U87MG.ΔEGFRvIII cells through a catheter placed 1 mm anterior and 4 mm lateral to bregma. Tumors were treated with an infusion of MR1-1-PE38 immunotoxin or saline control through the catheter directly into the tumor. The immunotoxin (0.2, 0.6 and 2.0 μg) was delivered in 200 μl of PBS with HSA over 7 days using an Alzet® osmotic pump as described in the previous Example. Treatment was initiated 3 days following tumor inoculation.

Figure 4:
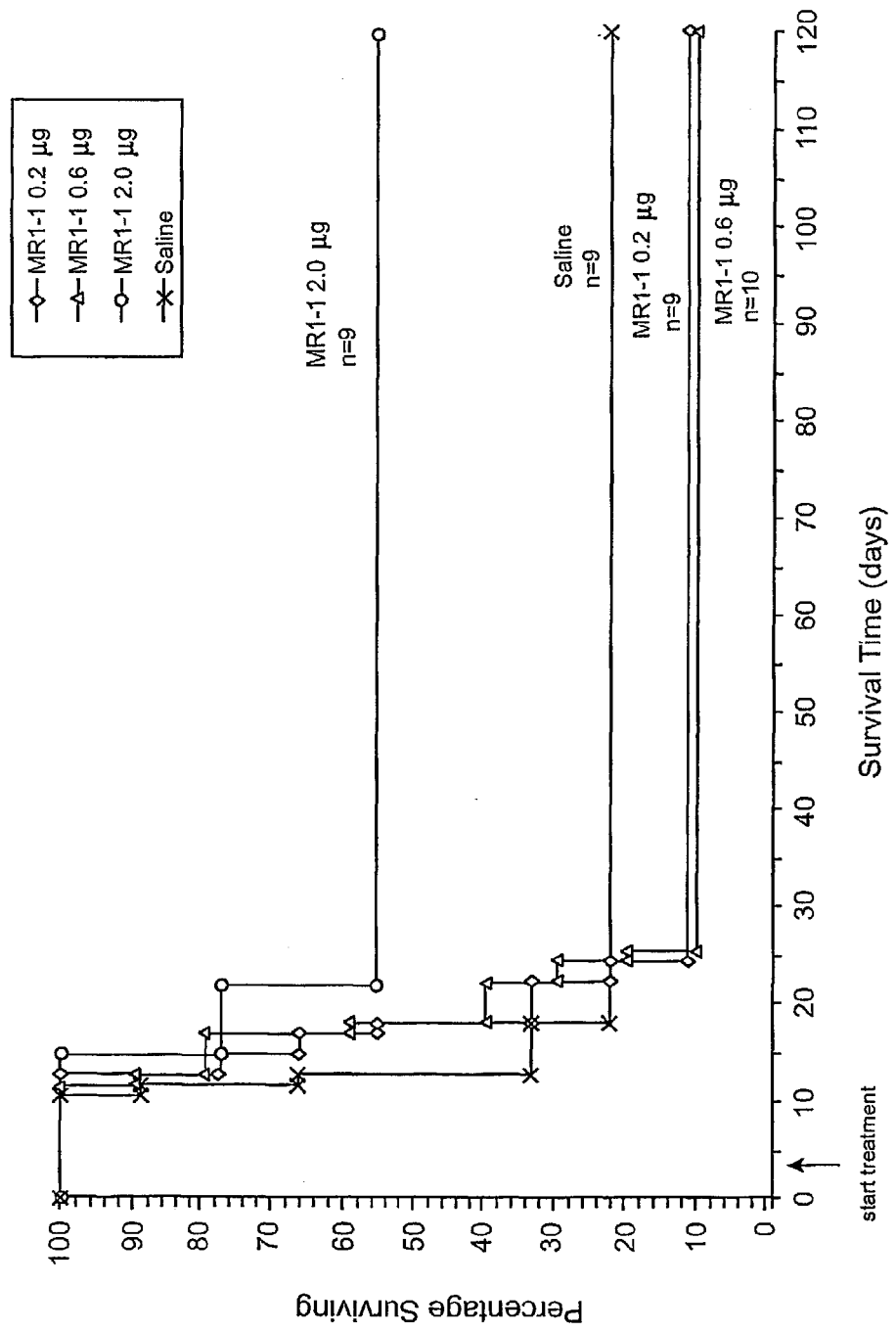
FIG. 4. Survival of athymic rats with intracranial tumors of human glioblastoma cells transfected with EGFRvIII and treated with MR-1-targeted immunotoxin or saline control. The Y-axis shows the percentage of animals surviving at a given point in time. The X-axis shows the survival time in days. Legend: MR1-1, denotes MR1-1-PE38 immunotoxin. Open diamonds, animals administered 0.2 μg of MR1-1-PE38 immunotoxin (in 200 μl of PBS with 0.2% HSA) over a 7 day period by 24 hour infusion. Open triangle: animals administered 0.6 μg of MR1-1-PE38 immunotoxin in the same manner. Open circle: animals administered 2.0 μg of MR1-1-PE38 immunotoxin in the same manner. "X," animals administered saline control in the same manner.

As shown in FIG. 4, only some ten percent of animals receiving the 0.2 or 0.6 μg doses of immunotoxin survived past day 25, while about 22% of the animals receiving the saline control survived. In contrast, of animals receiving the 2 μg dose, about 55%, survived, more than double the percentage survival of the animals receiving the saline control. The results suggest that the 0.2 and 0.6 μg doses were too low to affect survival, while the 2.0 μg dose of immunotoxin significantly prolonged survival.

Example 7

EGFRvIII neoplastic meningitis was initiated in athymic rats by the injection of $5 \times 10^6$ U87MG.ΔEGFRvIII cells in 40 μl of PBS-HSA solution through an indwelling intrathecal catheter. Treatment of all tumor-bearing animals started 3 days after tumor inoculation. The MR1-1-PE38 immunotoxin was given in 40 μl of PBS-HSA on days 3, 5 and 7 after tumor initiation. Control animals were administered 40 μl of PBS-HSA on the same days.

Figure 5:
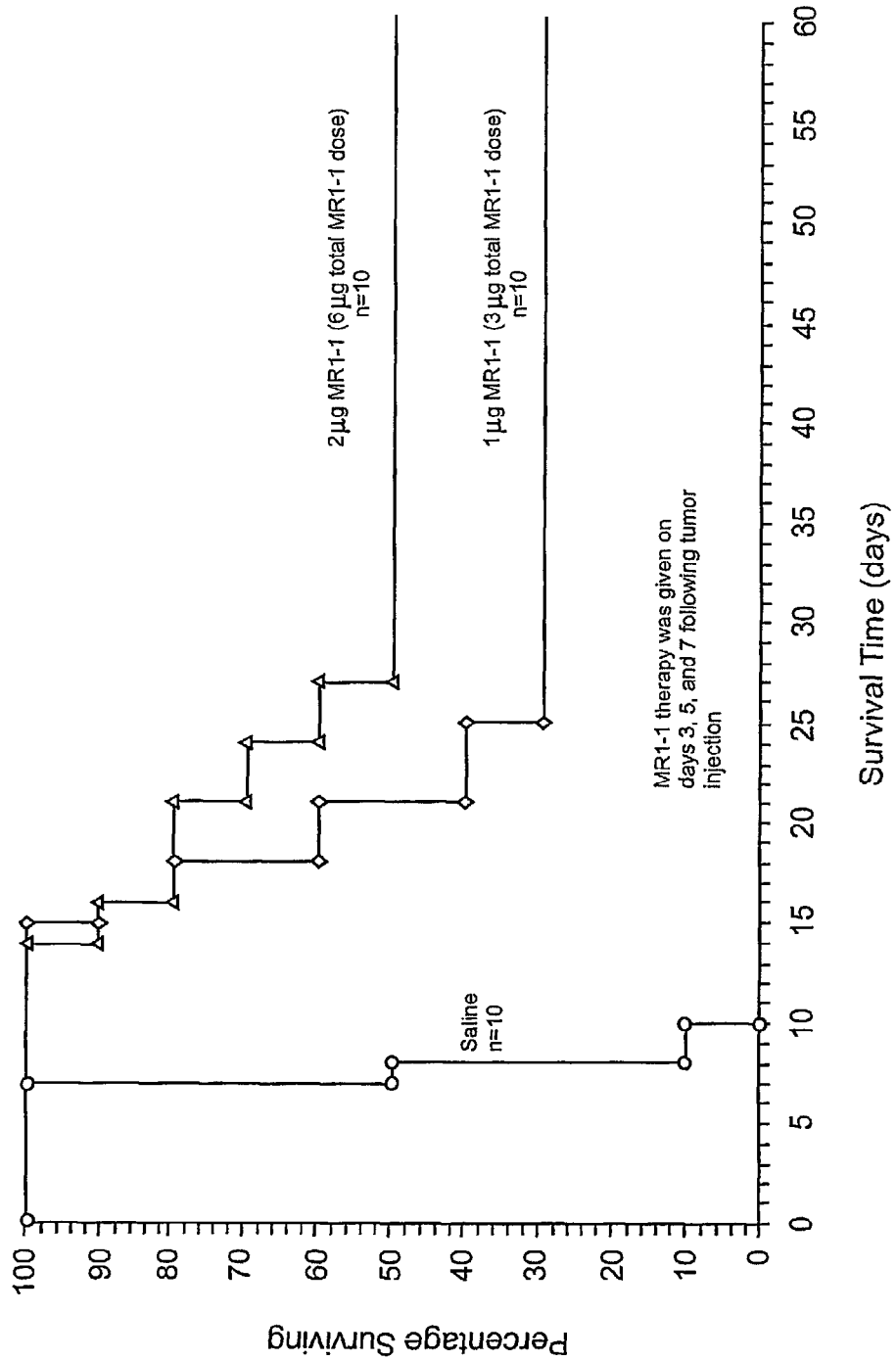
FIG. 5. Survival of athymic rats with neoplastic meningitis from intrathecal injection of human glioblastoma cells transfected with EGFRvIII and treated with MR1-1-targeted immunotoxin or saline control. The Y-axis shows the percentage of animals surviving at a given point in time. The X-axis shows the survival time in days. Legend: MR1-1 denotes MR1-1-PE38 immunotoxin. Triangles: Animals administered 2 μg of MR-1-1-PE38 immunotoxin in 40 μl of PBS with 0.2% HA on days 3, 5, and 7 after tumor initiation, for a total dose of 6 μg. Diamonds: Animals administered 1 μg of MR1-1-PE38 immunotoxin in 40 μl of PBS with 0.2% HA on days 3, 5, and 7 after tumor initiation, for a total dose of 3 μg of immunotoxin. Circles: Animals administered 40 μl of PBS with 0.2% HA on days 3, 5, and 7 after tumor initiation, as controls.

As shown in FIG. 5, all the animals receiving the saline control were dead by day 10. In contrast, all animals receiving the immunotoxin had their survival prolonged to at least until day 14, with 30% of the animals receiving the 1 μg dose and 50% of the animals receiving the 2 μg dose surviving through day 60.

Example 8

Tumors were initiated in athymic mice by the injection of 50 μl of U87MG.ΔEGFRvIII tumor cell homogenate seven days before the start of treatment (the start of treatment was designated as day "0" for this study). The tumors were treated with three 20 μl intratumoral bolus injections of MR1-1-PE38 immunotoxin at doses of 1, 2, or 3 μg, or of a saline control (the PBS-HSA solution described in the preceding Examples) on days 0, 2, and 4. Tumors had an average volume of 600 mm³ at the start of treatment on day 0.

Figure 6:
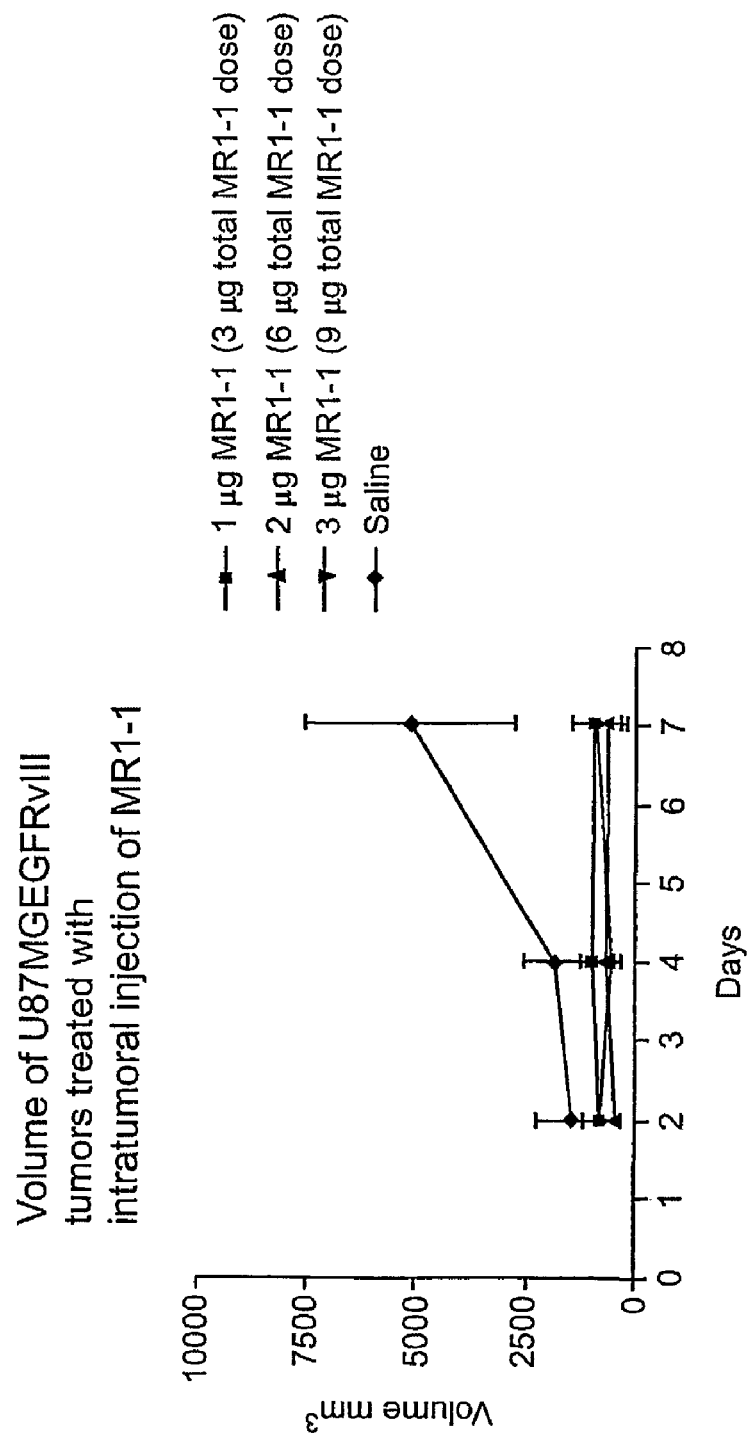
FIG. 6. Volume of tumors over time in athymic mice injected in right flank with human glioblastoma cells transfected with EGFRvIII and treated with MR1-1-targeted immunotoxin or saline control. The Y-axis shows the tumor volume in $mm^3$. The X-axis shows the time in days from initiation of treatment (the animals were injected with the tumor cells 7 days before day "0"). Legend: MR1-1 denotes MR1-1-PE38 immunotoxin. Squares: Animals administered with 1 μg bolus injections of MR1-1-PE38 immunotoxin in 20 μl on days 0, 2, and 4, for a total dose of 3 μg. Right-side up triangles: Animals administered 2 μg bolus injections of MR1-1-PE38 immunotoxin in 20 μl saline on days 0, 2, and 4, for a total dose of 6 μg of immunotoxin. Upside down triangles: Animals administered 3 μg bolus injections of MR1-1-PE38 immunotoxin in 20 μl saline on days 0, 2, and 4, for a total dose of 9 μg of immunotoxin. Diamonds: Animals administered 20 μl bolus injections of saline on days 0, 2, and 4, as controls.

As shown on FIG. 6, the tumor sizes of the animals treated with any of the immunotoxin doses remained approximately the same as measured on day 2 following the first treatment, effectively arresting growth of the tumor. In contrast, animals treated only with the saline control showed a rapid increase in tumor load, with tumor volume increasing up to as much as 7500 m³ by day 7.

All publications and patents mentioned in this specification are herein incorporated by reference into the specification to the same extent as if each individual publication or patent was specifically and individually indicated to be incorporated herein by reference.

TABLE 3

Phage Enrichment During Panning

| Panning Round | Phage Input | Phage Eluted |
|---|---|---|
| $V_H$CDR3 | | |
| 1 | $3 \times 10^9$ | $1.5 \times 10^5$ |
| 2 | $3 \times 10^{11}$ | $1.0 \times 10^6$ |
| 3 | $5 \times 10^{11}$ | $1.5 \times 10^8$ |
| 4 | $5 \times 10^{11}$ | $2.0 \times 10^7$ |
| $V_L$CDR3 | | |
| 1 | $1 \times 10^{10}$ | $2.4 \times 10^5$ |
| 2 | $1 \times 10^{10}$ | $5.5 \times 10^6$ |
| 3 | $1 \times 10^{10}$ | $2.0 \times 10^7$ |

TABLE 4

| Immunotoxin | Experiment 1 $IC_{50}$ | Experiment 2 $IC_{50}$ |
|---|---|---|
| MR1(Fv)-PE38 | 9.2 ± 2.1 | 6.6 ± .2 |
| MR1(Fv)($V_H$S98P-T99Y)-PE38 | 6.0 ± .39 | 4.6 ± .7 |
| MR1-1(Fv)-PE38 | 2.6 ± 6.2 | 2.0 ± 1 |

Comparison of the cytotoxic activity of MR1(Fv)-PE38 with two mutants with increased affinity for EGFRvIII. $IC_{50}$s are calculated from assays using different amounts of immunotoxins. The values are the means±S.D. P values are <0.01 when comparing MRI(Fv)-PE38 with MR1-1(Fv)-PE38 and MR1(Fv)($V_H$S$^{98}$P-T$^{99}$Y)-PE38 with MR1-1(Fv)-PE38 in experiment 1 and when comparing MR1(Fv)-PE38 with MR1(Fv)($V_H$S98P-T99Y)-PE38, and MR 1 (FV)($V_H$S98P-T99Y)-PE38 with MR 1-1 (Fv)-PE38 in experiment 2.

TABLE 5

DNA and Amino Acid Sequence of Heavy Chain CDR3 and Light chain CDR3 of MR1 Fv*

| MR1 CDR3H | GGC | TAT | TCT | AGT | ACC | TCT | TAT | GCT | ATG | (SEQ ID NO: 10) |
|---|---|---|---|---|---|---|---|---|---|---|
| | G | Y | S | S | T | S | Y | A | M | (SEQ ID NO: 8) |
| Position | 95 | 96 | 97 | 98 | 99 | 100 | 100A | 100B | 100C | |
| MR1 CDR3L | TTG | CAA | AGT | TTT | AAC | GTG | CCT | CTT | ACA | (SEQ ID NO: 11) |
| | L | Q | S | F | N | V | P | L | T | (SEQ ID NO: 9) |
| Position | 89 | 90 | 91 | 92 | 93 | 94 | 95 | 96 | 97 | |

*Hot spots having the sequence Pu G Py A/T are underlined.

TABLE 6

Sequences and Properties of Mutant Phage Isolated from Heavy Chain CDR3 (SEQ ID NO: 8) Library and of Immunotoxins Made with the Mutant scFvs

| Position | 95 | 96 | 97 | 98 | 99 | 100 | 100A | 100B | 100C | # out of 22 | IC50 ng/ml | KD nM | Yield % |
|---|---|---|---|---|---|---|---|---|---|---|---|---|---|
| Original Amino Acid | G | Y | S | S | T | S | Y | A | M | | 8.0 | 8.0 | 2.0 |
| 3rd Round Residues | | | | S | T* | | | | | 5 | 8.0 | 8.0 | 2.0 |
| | | | | P | S | | | | | 4 | 8.0 | N.D. | 17.5 |
| | | | | P | Y | | | | | 3 | 3.5 | 6.0 | 7.0 |
| | | | | P | N | | | | | 2 | 4.5 | 11.0 | 10.0 |
| | | | | P | W | | | | | 2 | 4.5 | 4.0 | 10.0 |
| | | | | A | D** | | | | | 2 | N.D. | N.D. | N.D. |
| | | | | P | I | | | | | 1 | 4.5 | 5.0 | 10.0 |
| | | | | W | F | | | | | 1 | 8.0 | N.D. | 10.0 |
| | | | | P | V | | | | | 1 | 6.5 | N.D. | 7.0 |
| | | | | | W | | | | | 1 | 8.0 | N.D. | 5.0 |
| | | | | P | | | | | | 1 | 8.0 | 8.0 | ? |
| | | | | | | | | | | #out of 10 | | | |
| 4th Round Residues | | | | S | T* | | | | | 1 | 8.0 | 8.0 | 2.0 |
| | | | | P | N | | | | | 3 | 4.5 | 11.0 | 10.0 |
| | | | | P | Y | | | | | 3 | 3.5 | 6.0 | 7.0 |
| | | | | P | F | | | | | 2 | 6.0 | 20.0 | 3.0 |
| | | | | P | W | | | | | 1 | 4.5 | 4.0 | 10.0 |

*Wild type
**Could not make immunotoxin

TABLE 7

Sequences and Properties of Mutant Phage Isolated from Light Chain CDR3 (SEQ ID NO: 9) Library and of Immunotoxins Made with the Mutant scFvs

| Position | 89 | 90 | 91 | 92 | 93 | 94 | 95 | 96 | 97 | # out of 17 | IC50 ng/ml | KD nM | Yield % |
|---|---|---|---|---|---|---|---|---|---|---|---|---|---|
| Original Amino Acid | L | Q | S | F | N | V | P | L | T | | 3.5 | 6 | 7 |
| 2$^{nd}$ Round Residues | | | S | F | | | | | | 4 | 3.5 | 6 | 7 |
| | | | S | W | | | | | | 6 | 1.3 | 3 | 7 |
| | | | S | R | | | | | | 3 | 6.0 | 9 | 8 |
| | | | S | S | | | | | | 2 | 15.0 | 22 | 16 |
| | | | S | L | | | | | | 1 | 5.5 | 4 | 5 |
| | | | S | M | | | | | | 1 | 9.0 | 6 | 2 |
| | | | | | | | | | | # out of 10 | | | |
| 3$^{RD}$ Round Residues | | | S | F | | | | | | 1 | 3.5 | 6 | 7 |
| | | | S | S | | | | | | 7 | 15.0 | 22 | 16 |
| | | | S | W | | | | | | 1 | 1.3 | 3 | 7 |
| | | | S | R | | | | | | 1 | 6.0 | 9 | 8 |

SEQUENCE LISTING

<160> NUMBER OF SEQ ID NOS: 11

<210> SEQ ID NO 1
<211> LENGTH: 46
<212> TYPE: PRT
<213> ORGANISM: Artificial Sequence
<220> FEATURE:
<223> OTHER INFORMATION: Description of Artificial Sequence:CDR3Hb DNA
      oligomer

<400> SEQUENCE: 1

Cys Thr Thr Gly Gly Cys Cys Cys Ala Ser Asn Ser Asn Asn
  1               5                  10                  15

Ser Asn Asn Ala Gly Ala Gly Gly Thr Ala Cys Thr Ala Gly Ala Ala
             20                  25                  30

Thr Ala Gly Cys Cys Thr Cys Thr Thr Gly Thr Gly Cys Ala
         35                  40                  45

<210> SEQ ID NO 2
<211> LENGTH: 46
<212> TYPE: PRT
<213> ORGANISM: Artificial Sequence
<220> FEATURE:
<223> OTHER INFORMATION: Description of Artificial Sequence: CDR3Hd DNA
      Oligomer

<400> SEQUENCE: 2

Cys Thr Thr Gly Gly Cys Cys Cys Ala Cys Ala Thr Ala Gly Cys
  1               5                  10                  15

Ala Thr Ala Ser Asn Asn Ser Asn Asn Ser Asn Asn Ala Gly Ala Ala
             20                  25                  30

Thr Ala Gly Cys Cys Thr Cys Thr Thr Gly Thr Gly Cys Ala
         35                  40                  45

<210> SEQ ID NO 3
<211> LENGTH: 46
<212> TYPE: PRT
<213> ORGANISM: Artificial Sequence
<220> FEATURE:
<223> OTHER INFORMATION: Description of Artificial Sequence: CDR3Hf DNA
      Oligomer -continued

```
<400> SEQUENCE: 3

Cys Thr Thr Gly Gly Cys Cys Cys Ala Cys Ala Thr Ala Gly Cys
  1               5                  10                  15

Ala Thr Ala Ala Gly Ala Gly Gly Thr Ala Cys Thr Ser Asn Asn Ser
                 20                  25                  30

Asn Asn Ser Asn Asn Thr Cys Thr Thr Gly Thr Gly Cys Ala
             35                  40                  45

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: S1 DNA
      oligomer

<400> SEQUENCE: 4

Cys Ala Ala Cys Gly Thr Gly Ala Ala Ala Ala Ala Thr Thr Ala
  1               5                  10                  15

Thr Thr Ala Thr Thr Cys Gly Cys
                 20

<210> SEQ ID NO 5
<211> LENGTH: 32
<212> TYPE: PRT
<213> ORGANISM: Artificial Sequence
<220> FEATURE:
<223> OTHER INFORMATION: Description of Artificial Sequence: AMBN DNA
      oligomer

<400> SEQUENCE: 5

Gly Cys Thr Ala Ala Ala Cys Ala Ala Cys Thr Thr Thr Cys Ala Ala
  1               5                  10                  15

Cys Ala Gly Thr Cys Thr Ala Thr Gly Cys Gly Gly Cys Ala Cys
                 20                  25                  30

<210> SEQ ID NO 6
<211> LENGTH: 39
<212> TYPE: PRT
<213> ORGANISM: Artificial Sequence
<220> FEATURE:
<223> OTHER INFORMATION: Description of Artificial Sequence: VLMUT DNA
      oligomer

<400> SEQUENCE: 6

Gly Ala Thr Thr Ala Cys Thr Ala Cys Thr Gly Thr Thr Thr Gly Cys
  1               5                  10                  15

Ala Ala Asn Asn Ser Asn Asn Ser Ala Ala Cys Gly Thr Gly Cys Cys
                 20                  25                  30

Thr Cys Thr Thr Ala Cys Ala
             35

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: EGFRvIII
      peptide
<220> FEATURE:
<221> NAME/KEY: MOD_RES
<222> LOCATION: (17)
<223> OTHER INFORMATION: Xaa = Lys modified by biotin

<400> SEQUENCE: 7
```

```
Leu Glu Glu Lys Lys Gly Asn Tyr Val Val Thr Asp His Ser Gly Gly
 1               5                  10                 15

Xaa

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence:
      Original phage amino acid, positions 95-100c

<400> SEQUENCE: 8

Gly Tyr Ser Ser Thr Ser Tyr Ala Met
 1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence:
      Original phage amino acid, positions 89-97

<400> SEQUENCE: 9

Leu Gln ser Phe Asn Val Pro Leu Thr
 1               5

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:
      Original phage amino acid, positions 95-100c

<400> SEQUENCE: 10
ggctattcta gtacctctta tgctatg                                            27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:
      Nucleic acid sequence relating to original phage amino
      acid, positions 89-97

<400> SEQUENCE: 11
ttgcaaagtt ttaacgtgcc tcttaca                                            27
```

What is claimed is:

1. An isolated polypeptide comprising an antibody heavy chain variable region ("VH") and an antibody light chain variable region ("VL"), each region comprising three complementarity determining regions ("CDRs"), which CDRs of each region are numbered sequentially CDR1 to CDR3 starting from the amino terminus, the polypeptide when made into an immunotoxin with a *Pseudomonas* exotoxin A or cytotoxic fragment thereof ("PE") forming an immunotoxin which binds to epidermal growth factor receptor type III ("EGFRvIII") antigen and which has a cytotoxicity to cells expressing said antigen at least equal to the cytotoxicity to said cells of an immunotoxin of parental antibody MR1 (SEQ ID NO.:18) and said PE, and a higher yield, when made into an immunotoxin with said PE, than that of MR1 when made into an immunotoxin with said PE, wherein:

(a) CDRs 1–3, respectively of the $V_H$ of the polypeptide have the sequence of CDRs 1–3, respectively of parental antibody MR1 $V_H$, except for:

(i) substitution of an amino acid selected from the group consisting of proline and tryptophan for the serine at position 98 of the CDR3 of the heavy chain variable region of antibody MR1, and (ii) substitution of an amino acid selected from the group consisting of: tyrosine, asparagine, tryptophan, isoleucine, phenylalanine, serine, and valine for the threonine at position 99 of the CDR3 of the heavy chain variable region of antibody MR 1 and, optionally, (iii) a substitution in CDR1 or CDR2 of said heavy chain variable region of at least one amino acid encoded by a codon that comprises a nucleotide belonging to a hot spot motif selected from AGY or RGYW, wherein R is A or G, Y is C or T and W is A or T; and (b) CDRs 1–3, respectively, of the $V_L$ of the polypeptide have:

(i) the sequence of CDRs 1–3, respectively, of antibody MR1 $V_L$ or, (ii) the sequence of CDRs 1–3, respectively, of antibody MR1 $V_L$ except for a substitution in one or more of said CDRs 1–3 of said polypeptide at least one amino acid encoded by a codon that comprises a nucleotide belonging to a hot spot motif selected from AGY or RGYW, wherein R is A or G, Y is C or T and W is A or T.

2. The polypeptide of claim 1, further comprising a substitution in CDR1 or CDR2 of said heavy chain variable region of at least one amino acid, the amino acid encoded by a codon that comprises a nucleotide belonging to a hot spot motif selected from AGY or RGYW, wherein R is A or G, Y is C or T and W is A or T.

3. The polypeptide of claim 1, further comprising a substitution in a CDR of said antibody light chain variable region of at least one amino acid, the amino acid encoded by a codon that comprises a nucleotide belonging to a hot spot motif selected from AGY or RGYW, wherein R is A or G, Y is C or T and W is A or T.

4. The polypeptide of claim 1, wherein the substitution occurs in CDR1 or CDR2 of said light chain variable region.

5. The polypeptide of claim 1, wherein said substitutions in said $V_H$ are selected from the group consisting of: S98P-T99Y, S98P-T99N, S98P-T99W, S98P-T99I, S98P-T99F, S98P-T99S, S98W-T99F, and S98P-T99V.

6. The polypeptide of claim 1, wherein said polypeptide is a scFv.

7. The polypeptide of claim 1, wherein said polypeptide is a dsFv, a Fab, or a F(ab')$_2$.

8. The polypeptide of claim 3, wherein the substitutions in the heavy chain variable region are S98P-T99Y and the substitution in the light chain variable region is F92W (antibody MR1-1).

9. A chimeric molecule comprising a polypeptide of claim 1, attached to an effector molecule, therapeutic moiety or a detectable label.

10. The chimeric molecule of claim 9, wherein the therapeutic moiety is a toxic moiety.

11. The chimeric molecule of claim 10, wherein the toxic moiety is a *Pseudomonas* exotoxin A ("PE") or a cytotoxic fragment thereof.

12. The chimeric molecule of claim 10, wherein the toxic moiety is a cytotoxic fragment, which is PE38.

13. The chimeric molecule of claim 11, wherein said chimeric molecule has an IC$_{50}$ of 7 ng/ml or lower.

14. The chimeric molecule of claim 11, wherein said chimeric molecule has an IC$_{50}$ of 5 ng/ml or lower.

15. The chimeric molecule of claim 11, wherein said chimeric molecule has an IC$_{50}$ of about 3.5 ng/ml.

16. The pelypeptide chimeric molecule of claim 11, wherein said substitution is wherein said substitutions in said $V_H$ are selected from the group consisting of: S98P-T99Y, S98P-T99N, S98P-T99W, S98P-T99I, S98P-T99F, S98P-T99S, S98W-T99F, and S98P-T99V.

17. The chimeric molecule of claim 11, wherein said chimeric molecule has a yield of about 7%.

18. The chimeric molecule of claim 10, wherein the toxic moiety is selected from the group consisting of diphtheria toxin or a cytotoxic fragment thereof, saporin or a cytotoxic fragment thereof, pokeweed antiviral toxin or a cytotoxic fragment thereof, ricin or a cytotoxic fragment thereof, and bryodin 1 or a cytotoxic fragment thereof.

19. The chimeric molecule of claim 11, wherein the substitutions in the heavy chain are S98P-T99Y and further comprising a substitution in the light chain variable region of F92W (antibody MR1-1).

20. The polypeptide of claim 1, fused to a filamentous phage pIII protein.

21. A method of killing a cell bearing epidermal growth factor receptor type III ("EGFRvIII"), comprising contacting the cell with an immunotoxin comprising a toxic moiety and a targeting moiety, the targeting moiety comprising a polypeptide comprising an antibody heavy chain variable region ("$V_H$") and an antibody light chain variable region ("$V_L$"), each region comprising three complementarity determining regions ("CDRs"), which CDRs of each region are numbered sequentially CDR1 to CDR3 starting from the amino terminus, the polypeptide, when made into an immunotoxin with a *Pseudomonas* exotoxin A or cytotoxic fragment thereof ("PE") forming an immunotoxin which binds to epidermal growth factor receptor type III ("EGFRvIII") antigen and which has a cytotoxicity to cells expressing said antigen at least equal to the cytotoxicity to said cells of an immunotoxin consisting of parental antibody MR1 (SEQ ID NO.:18) when made into an immunotoxin with said PE, and a higher yield, when made into an immunotoxin with said PE, than that of parental antibody MR1 (SEQ ID NO.:18) when made into an immunotoxin with said PE, wherein:

(a) CDRs 1–3, respectively of the $V_H$ of the polypeptide have the sequence of CDRs 1–3, respectively of parental antibody MR1 (SEQ ID NO.:18) $V_H$, except for:

(i) substitution of an amino acid selected from the group consisting of proline and tryptophan for the serine at position 98 of the CDR3 of the heavy chain variable region of antibody MR1, and (ii) substitution of an amino acid selected from the group consisting of: tyrosine, asparagine, tryptophan, isoleucine, phenylalanine, serine, and valine for the threonine at position 99 of the CDR3 of the heavy chain variable region of antibody MR1 and, optionally, (iii) a substitution in CDR1 or CDR2 of said heavy chain variable region of at least one amino acid encoded by a codon that comprises a nucleotide belonging to a hot spot motif selected from AGY or RGYW, wherein R is A or G, Y is C or T and W is A or T; and (b) CDRs 1–3, respectively, of the $V_L$ of the polypeptide have:

(i) the sequence of CDRs 1–3, respectively, of antibody MR1 $V_L$ or, (ii) the sequence of CDRs 1–3, respectively, of antibody MR1 $V_L$ except for a substitution in one or more of said CDRs 1–3 of said polypeptide at least one amino acid encoded by a codon that comprises a nucleotide belonging to a hot spot motif selected from AGY or RGYW, wherein R is A or G, Y is C or T and W is A or T.

22. The method of claim 21, wherein said polypeptide further comprises a substitution in CDR1 or CDR2 of said heavy chain variable region of at least one amino acid, the amino acid encoded by a codon that comprises a nucleotide belonging to a hot spot motif selected from AGY or RGYW, wherein R is A or G, Y is C or T and W is A or T.

23. The method of claim 21, wherein said antibody further comprises a substitution in a CDR of said light chain variable region of at least one amino acid, the amino acid encoded by a codon that comprises a nucleotide belonging to a hot spot motif selected from AGY or RGYW, wherein R is A or G, Y is C or T and W is A or T.

24. The method of claim 23, wherein the CDR3 mutated light chain variable region comprises a tryptophan substituted for a phenylalanine at position 92.

25. The method of claim 21, wherein the targeting moiety is antibody MR1-1.

26. The method of claim 21, wherein the cell is a malignant cell.

27. The method of claim 21, wherein the malignant cell is a glioma cell.

28. The method of claim 21, wherein the malignant cell is a breast carcinoma cell.

29. The method of claim 21, wherein the malignant cell is a lung carcinoma cell.

30. The method of claim 21, wherein the malignant cell is a ovarian carcinoma cell.

* * * * *

UNITED STATES PATENT AND TRADEMARK OFFICE
CERTIFICATE OF CORRECTION

PATENT NO. : 7,129,332 B2
APPLICATION NO. : 10/203675
DATED : October 31, 2006
INVENTOR(S) : Ira Pastan et al.

It is certified that error appears in the above-identified patent and that said Letters Patent is hereby corrected as shown below:

In Specification

Column 41, Line 20-65 - Column 46, the Sequence Listing on the patent has been replaced with the corrected Sequence Listing as shown on the attached pages.

```
<110> Pastan, Ira
      Beers, Richard
      Partha, Chowdhury S.
      Darell, Bigner
      The Government of the United States of America
          as represented by The Secretary of the
          Department of Health and Human Services
      Duke University <120> Anti-EGFRvIII scFvs With Improved Cytotoxicity and
      Yield, Immunotoxins Based Thereon, and Methods of Use
      Thereof

<130> 015280-419100US

<140> US 10/203,675
<141> 2002-08-09

<150> US 60/185,039
<151> 2000-02-25

<150> WO PCT/US01/05923
<151> 2001-02-23

<160> 18

<170> PatentIn Ver. 2.1
```

Signed and Sealed this
Eighteenth Day of February, 2014

Michelle K. Lee
*Deputy Director of the United States Patent and Trademark Office*

<210> 1
<211> 46
<212> DNA
<213> Artificial Sequence

<220>
<223> Description of Artificial Sequence:CDR3Hb DNA
    oligomer two-step PCR upstream primer for
    randomization in heavy chain CDR3

<220>
<221> modified_base
<222> (1)..(46)
<223> n = g, a, c or t

<400> 1
cttggcccca snnsnnsnna gaggtactag aatagcctct tgtgca      46

<210> 2
<211> 46
<212> DNA
<213> Artificial Sequence

<220>
<223> Description of Artificial Sequence:CDR3Hd DNA
    oligomer two-step PCR upstream primer for
    randomization in heavy chain CDR3

<400> 4
caacgtgaaa aaattattat tcgc                              24

<210> 5
<211> 32
<212> DNA
<213> Artificial Sequence

<220>
<223> Description of Artificial Sequence:AMBN DNA
    oligomer two-step PCR downstream primer for
    randomization in heavy chain CDR3

<400> 5
gctaaacaac tttcaacagt ctatgcgggc ac                     32

<210> 6
<211> 39
<212> DNA
<213> Artificial Sequence

<220>
<221> modified_base
<222> (1)..(46)
<223> n = g, a, c or t

<400> 2
cttggcccca catagcatas nnsnnsnnag aatagcctct tgtgca      46

```
<210> 3
<211> 46
<212> DNA
<213> Artificial Sequence

<220>
<223> Description of Artificial Sequence:CDR3Hf DNA
      oligomer two-step PCR upstream primer for
      randomization in heavy chain CDR3

<220>
<221> modified_base
<222> (1)..(46)
<223> n = g, a, c or t

<400> 3
cttggcccca catagcataa gaggtactsn nsnnsnntct tgtgca                    46

<210> 4
<211> 24
<212> DNA
<213> Artificial Sequence

<220>
<223> Description of Artificial Sequence:S1 DNA oligomer
      two-step PCR upstream primer for randomization in
      heavy chain CDR3

<400> 9
Leu Gln Ser Phe Asn Val Pro Leu Thr
  1               5

<210> 10
<211> 27
<212> DNA
<213> Artificial Sequence

<220>
<223> Description of Artificial Sequence:DNA sequence of
      first 9 of eleven amino acids of original heavy
      chain V-H CDR3 of MR1 Fv, positions 95-100C <400> 10
ggctattcta gtacctctta tgctatg                                         27

<210> 11
<211> 27
<212> DNA
<213> Artificial Sequence

<220>
<223> Description of Artificial Sequence:DNA sequence of
      first 9 of eleven amino acids of original light
      chain V-L CDR3 of MR1 Fv, positions 89-97

<400> 11
ttgcaaagtt ttaacgtgcc tcttaca                                         27
```

```
<210> 12
<211> 5
<212> PRT
<213> Artificial Sequence

<220>
<223> Description of Artificial Sequence:single chain Fv
      (scFv) antibody peptide linker <400> 12
Gly Gly Gly Gly Ser
 1               5

<210> 13
<211> 5
<212> PRT
<213> Artificial Sequence

<220>
<223> Description of Artificial Sequence:native
      Pseudomonas exotoxin (PE) signal sequence to
      direct molecule into cytosol <400> 13
Arg Glu Asp Leu Lys
 1               5

<210> 14
<211> 4
<212> PRT
<213> Artificial Sequence

<220>
<223> Description of Artificial Sequence:signal sequence
      to direct molecule into cytosol <400> 14
Lys Asp Glu Leu
 1

<210> 15
<211> 4
<212> PRT
<213> Artificial Sequence

<220>
<223> Description of Artificial Sequence:signal sequence
      to direct molecule into cytosol <400> 15
Arg Asp Glu Leu
 1

<210> 16
<211> 4
<212> PRT
<213> Artificial Sequence
```

```
<220>
<223> Description of Artificial Sequence:C-terminal
      signal sequence to direct molecule into cytosol <400> 16
Lys Asp Glu Leu
  1

<210> 17
<211> 726
<212> DNA
<213> Mus musculus

<220>
<221> CDS
<222> (1)..(726)
<223> epidermal growth factor receptor antibody MR1
      single chain Fv (scFv) cDNA, partial CDS <220>
<221> misc_feature
<222> (1)..(362)
<223> encodes heavy chain variable domain <220>
<221> misc_feature
<222> (363)..(405)
<223> encodes linker sequence <220>
<221> misc_feature
<222> (406)..(726)
<223> encodes light chain variable domain <400> 17
cag gtg aaa ctg cag cag tct ggg gga ggc tta gtg aag cct gga gcg     48
Gln Val Lys Leu Gln Gln Ser Gly Gly Gly Leu Val Lys Pro Gly Ala
  1               5                  10                  15 tct ctg aaa ctc tcc tgt gta acc tct gga ttc act ttc aga aaa ttt     96
Ser Leu Lys Leu Ser Cys Val Thr Ser Gly Phe Thr Phe Arg Lys Phe
             20                  25                  30 ggc atg tct tgg gtt cgc cag act tca gac aag agg ctg gaa tgg gtc    144
Gly Met Ser Trp Val Arg Gln Thr Ser Asp Lys Arg Leu Glu Trp Val
         35                  40                  45 gca tcc att agt act ggc ggt tat aat acc tac tat tca gac aat gta    192
Ala Ser Ile Ser Thr Gly Gly Tyr Asn Thr Tyr Tyr Ser Asp Asn Val
     50                  55                  60 aag ggc cga ttc acc atc tcc aga gag aat gcc aag aac acc ctg tac    240
Lys Gly Arg Phe Thr Ile Ser Arg Glu Asn Ala Lys Asn Thr Leu Tyr
 65                  70                  75                  80 ctg caa atg agt agt ctg aag tct gag gac acg gcc ttg tat tac tgt    288
Leu Gln Met Ser Ser Leu Lys Ser Glu Asp Thr Ala Leu Tyr Tyr Cys
                 85                  90                  95
```

```
aca aga ggc tat tct agt acc tct tat gct atg gac tac tgg ggc caa        336
Thr Arg Gly Tyr Ser Ser Thr Ser Tyr Ala Met Asp Tyr Trp Gly Gln
            100                 105                 110 ggg acc acg gtc acc gtc tcc tca agt gga ggc ggt tca ggc gga ggt        384
Gly Thr Thr Val Thr Val Ser Ser Ser Gly Gly Gly Ser Gly Gly Gly
            115                 120                 125 ggc tct ggc ggt ggc gga tcg gac atc gag ctc act cag tct cca gca        432
Gly Ser Gly Gly Gly Gly Ser Asp Ile Glu Leu Thr Gln Ser Pro Ala
            130                 135                 140 tcc ctg tcc gtg gct aca gga gaa aaa gtc act atc aga tgc atg acc        480
Ser Leu Ser Val Ala Thr Gly Glu Lys Val Thr Ile Arg Cys Met Thr
145                 150                 155                 160 agc act gat att gat gat gat atg aac tgg tac cag cag aag cca ggg        528
Ser Thr Asp Ile Asp Asp Asp Met Asn Trp Tyr Gln Gln Lys Pro Gly
                165                 170                 175 gaa cct cct aag ttc ctt att tca gaa ggc aat act ctt cgt cct gga        576
Glu Pro Pro Lys Phe Leu Ile Ser Glu Gly Asn Thr Leu Arg Pro Gly
            180                 185                 190 gtc cca tcc cga ttt tcc agc agt ggc act ggc aca gat ttt gtt ttt        624
Val Pro Ser Arg Phe Ser Ser Ser Gly Thr Gly Thr Asp Phe Val Phe
            195                 200                 205 aca att gaa aac aca ctc tcg gaa gat gtt gga gat tac tac tgt ttg        672
Thr Ile Glu Asn Thr Leu Ser Glu Asp Val Gly Asp Tyr Tyr Cys Leu
210                 215                 220 caa agt ttt aac gtg cct ctt aca ttc ggt gat ggc acc aag ctg gaa        720
Gln Ser Phe Asn Val Pro Leu Thr Phe Gly Asp Gly Thr Lys Leu Glu
225                 230                 235                 240 atc aaa                                                                 726
Ile Lys <210> 18
<211> 242
<212> PRT
<213> Mus musculus <220>
<223> epidermal growth factor receptor antibody MR1
      single chain Fv (scFv)

<400> 18
Gln Val Lys Leu Gln Gln Ser Gly Gly Gly Leu Val Lys Pro Gly Ala
1               5                   10                  15

Ser Leu Lys Leu Ser Cys Val Thr Ser Gly Phe Thr Phe Arg Lys Phe
                20                  25                  30

Gly Met Ser Trp Val Arg Gln Thr Ser Asp Lys Arg Leu Glu Trp Val
            35                  40                  45
```

```
Ala Ser Ile Ser Thr Gly Gly Tyr Asn Thr Tyr Tyr Ser Asp Asn Val
     50                  55                  60
Lys Gly Arg Phe Thr Ile Ser Arg Glu Asn Ala Lys Asn Thr Leu Tyr
 65              70                  75                       80
Leu Gln Met Ser Ser Leu Lys Ser Glu Asp Thr Ala Leu Tyr Tyr Cys
             85                  90                      95
Thr Arg Gly Tyr Ser Ser Thr Ser Tyr Ala Met Asp Tyr Trp Gly Gln
            100                 105                 110
Gly Thr Thr Val Thr Val Ser Ser Gly Gly Gly Ser Gly Gly Gly
        115                 120                 125
Gly Ser Gly Gly Gly Gly Ser Asp Ile Glu Leu Thr Gln Ser Pro Ala
    130                 135                 140
Ser Leu Ser Val Ala Thr Gly Glu Lys Val Thr Ile Arg Cys Met Thr
145                 150                 155                 160
Ser Thr Asp Ile Asp Asp Asp Met Asn Trp Tyr Gln Gln Lys Pro Gly
            165                 170                 175
Glu Pro Pro Lys Phe Leu Ile Ser Glu Gly Asn Thr Leu Arg Pro Gly
            180                 185                 190
Val Pro Ser Arg Phe Ser Ser Ser Gly Thr Gly Thr Asp Phe Val Phe
        195                 200                 205
Thr Ile Glu Asn Thr Leu Ser Glu Asp Val Gly Asp Tyr Tyr Cys Leu
    210                 215                 220
Gln Ser Phe Asn Val Pro Leu Thr Phe Gly Asp Gly Thr Lys Leu Glu
225                 230                 235                 240
Ile Lys
```